(12) United States Patent
Chu

(10) Patent No.: US 9,402,706 B2
(45) Date of Patent: Aug. 2, 2016

(54) BODILY IMPLANTS AND METHODS OF ADJUSTING THE SAME

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 343 days.

(21) Appl. No.: 13/190,240

(22) Filed: Jul. 25, 2011

(65) Prior Publication Data

US 2012/0029275 A1 Feb. 2, 2012

Related U.S. Application Data

(60) Provisional application No. 61/368,787, filed on Jul. 29, 2010.

(51) Int. Cl.
| | | |
|---|---|---|
| *A61F 2/00* | (2006.01) |
| *A61F 2/02* | (2006.01) |
| *A61B 17/06* | (2006.01) |
| A61B 17/04 | (2006.01) |
| A61B 17/00 | (2006.01) |
| A61M 5/34 | (2006.01) |

(52) U.S. Cl.
CPC ........... *A61F 2/0045* (2013.01); *A61B 17/0483* (2013.01); *A61B 17/06109* (2013.01); *A61B 17/06166* (2013.01); *A61B 17/06061* (2013.01); *A61B 2017/00353* (2013.01); *A61B 2017/00805* (2013.01); *A61B 2017/0414* (2013.01); *A61B 2017/0496* (2013.01); *A61B 2017/06042* (2013.01); *A61F 2220/0016* (2013.01); *A61F 2250/0007* (2013.01); *A61M 2005/342* (2013.01)

(58) Field of Classification Search
CPC ............... A61B 17/04; A61B 17/0404; A61B 17/0414; Y10S 606/903
USPC .......... 600/37, 29, 30; 128/897–899; 606/233
See application file for complete search history.

(56) References Cited

U.S. PATENT DOCUMENTS

| | | | |
|---|---|---|---|
| 5,562,689 A | 10/1996 | Green et al. |
| 6,063,106 A * | 5/2000 | Gibson | ......................... 606/232 |

(Continued)

FOREIGN PATENT DOCUMENTS

| | | |
|---|---|---|
| EP | 1800619 A1 | 6/2007 |
| WO | 9835616 A1 | 8/1998 |

(Continued)

OTHER PUBLICATIONS

Search Report and Written Opinion for International Application No. PCT/US2011/45395, mailed Nov. 26, 2012, 33 pages.

*Primary Examiner* — Catherine B Kuhlman
*Assistant Examiner* — Shannon McBride
(74) *Attorney, Agent, or Firm* — Brake Hughes Bellermann LLP

(57) ABSTRACT

A medical device includes a support member, a tether, and a retainer. The support member is configured to be placed within a body of a patient and provide support to a portion of the body of the patient. The tether forms a loop and is coupled to the support member. The tether is configured to extend from the body of the patient when the support member is placed within the body of the patient. The retainer is configured to be coupled to the tether at a first location on the tether and at a second location on the tether different than the first location. The retainer is configured to be disposed outside of the body of the patient when the support member is placed within the body of the patient.

16 Claims, 17 Drawing Sheets

(56) References Cited

U.S. PATENT DOCUMENTS

| | | | |
|---|---|---|---|
| 6,093,201 A * | 7/2000 | Cooper et al. | 606/232 |
| 6,106,545 A * | 8/2000 | Egan | 606/232 |
| 6,273,852 B1 | 8/2001 | Lehe et al. | |
| 6,652,562 B2 * | 11/2003 | Collier et al. | 606/232 |
| 6,881,184 B2 * | 4/2005 | Zappala | 600/29 |
| 7,326,213 B2 * | 2/2008 | Benderev et al. | 606/139 |
| 7,828,969 B2 | 11/2010 | Eaton et al. | |
| 2002/0147382 A1 * | 10/2002 | Neisz et al. | 600/29 |
| 2003/0065402 A1 * | 4/2003 | Anderson et al. | 623/23.66 |
| 2008/0132753 A1 * | 6/2008 | Goddard | 600/37 |
| 2008/0200751 A1 | 8/2008 | Browning | |
| 2009/0137861 A1 * | 5/2009 | Goldberg | A61B 17/0493 600/30 |
| 2009/0171139 A1 * | 7/2009 | Chu | 600/37 |
| 2009/0221867 A1 * | 9/2009 | Ogdahl et al. | 600/37 |
| 2009/0221868 A1 * | 9/2009 | Evans | 600/37 |
| 2010/0191044 A1 * | 7/2010 | Gobron et al. | 600/37 |
| 2010/0261950 A1 * | 10/2010 | Lund et al. | 600/30 |
| 2011/0172589 A1 * | 7/2011 | Finkelstein | A61B 17/3478 604/22 |

FOREIGN PATENT DOCUMENTS

| | | |
|---|---|---|
| WO | 2006108145 A1 | 10/2006 |
| WO | 2011060788 A1 | 5/2011 |
| WO | 2012015828 A2 | 2/2012 |
| WO | 2012015828 A3 | 2/2012 |

* cited by examiner

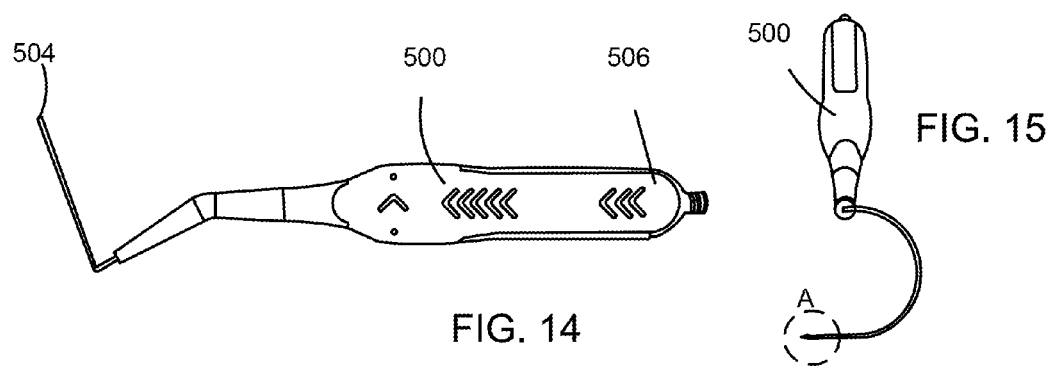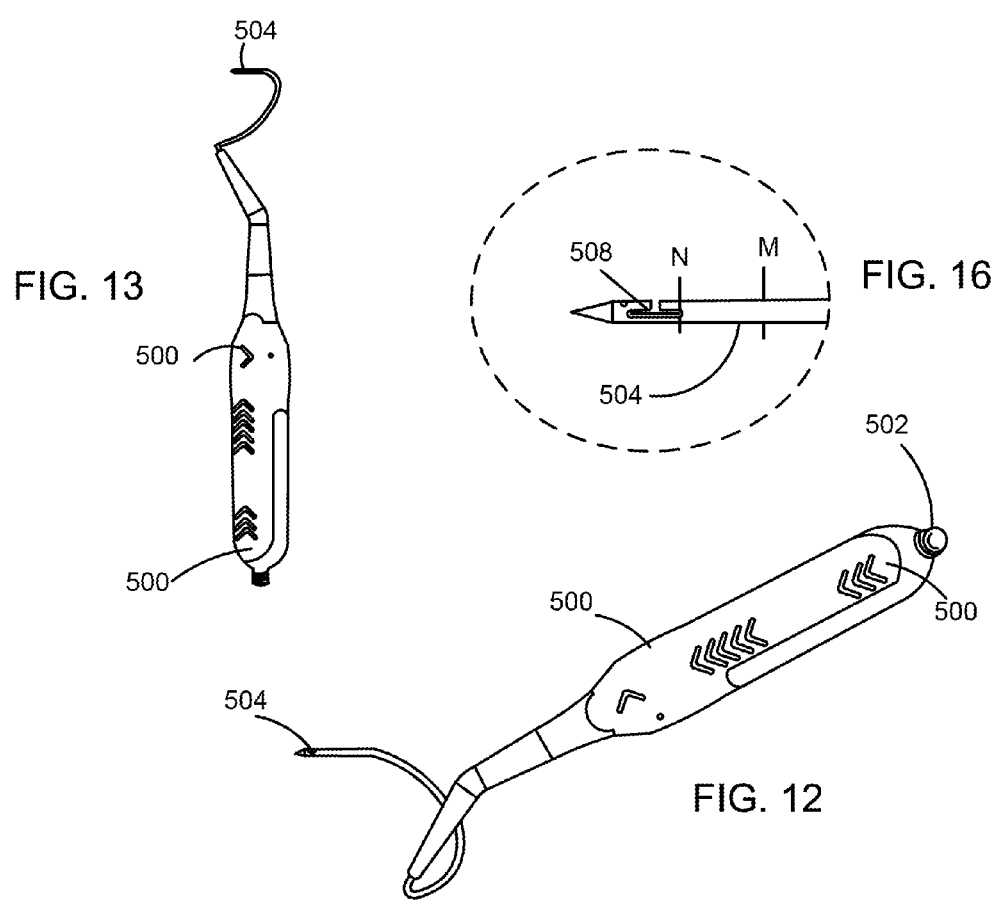

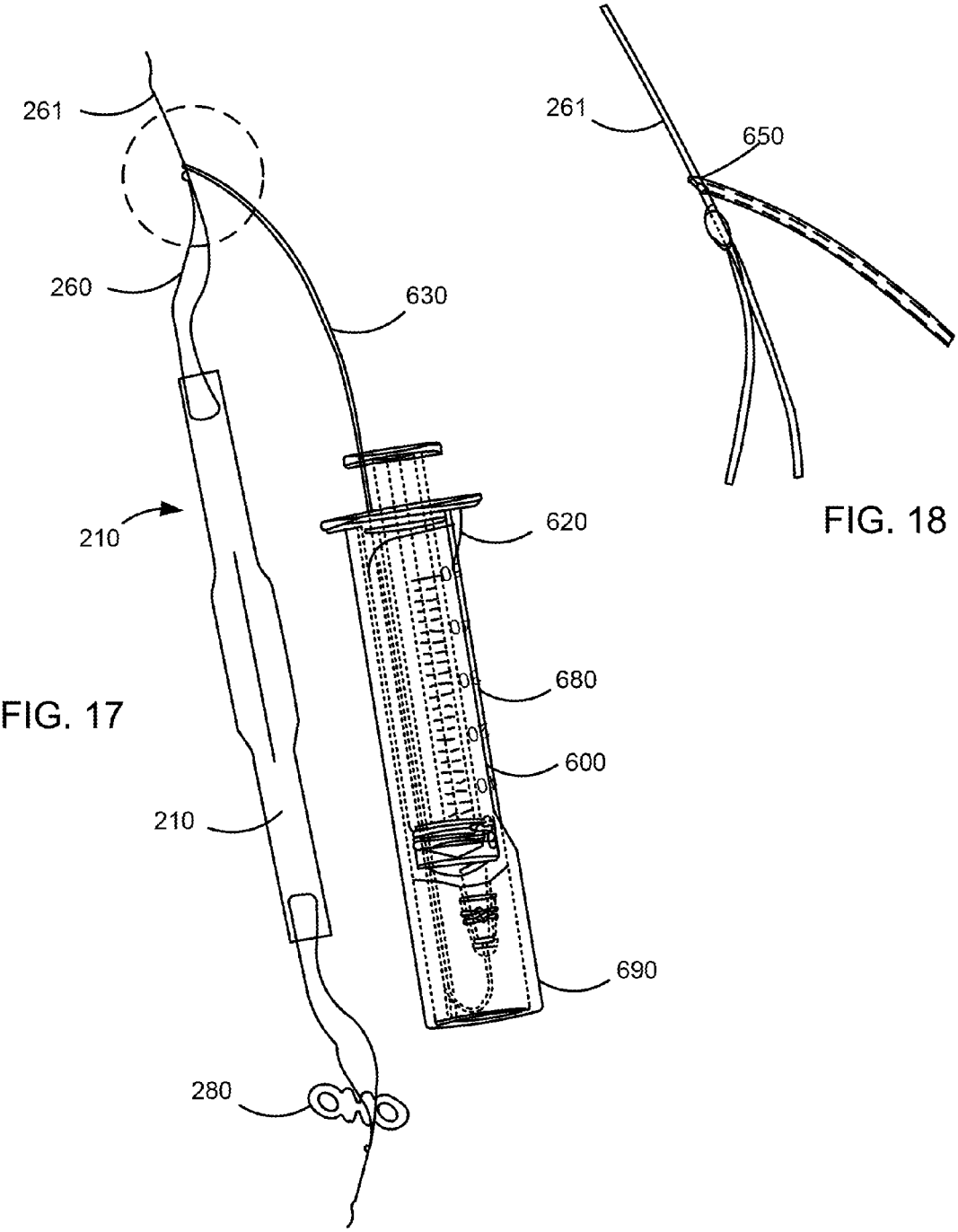

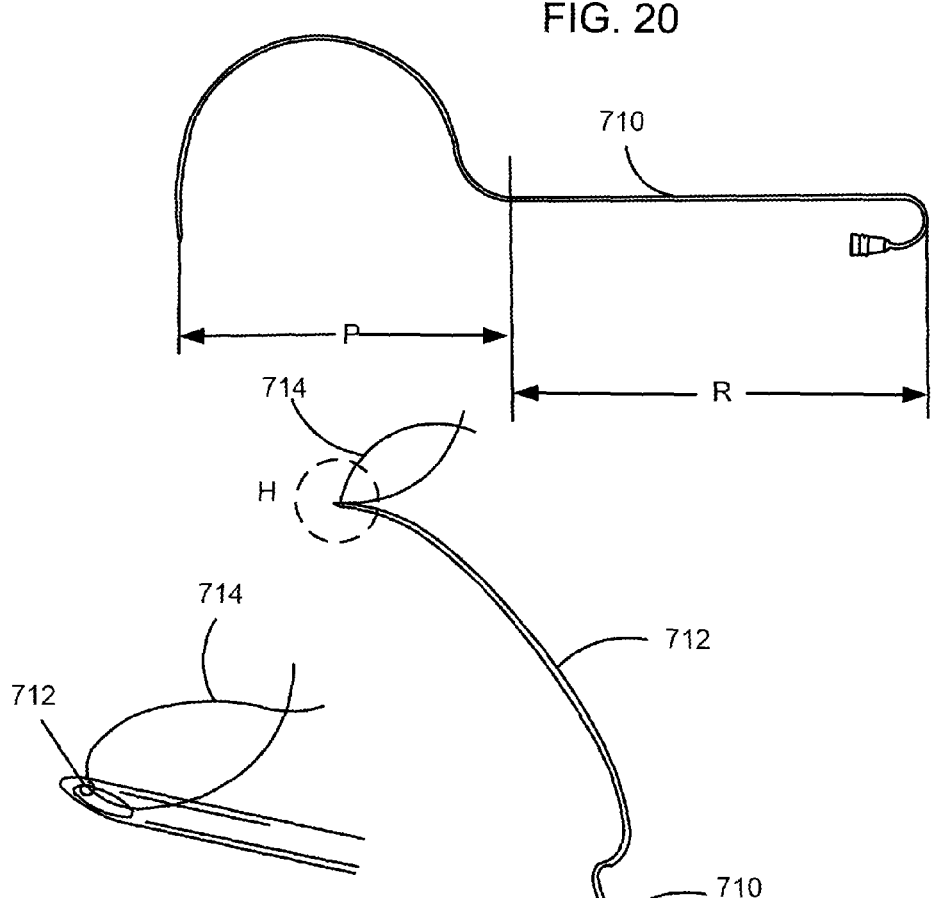
FIG. 20
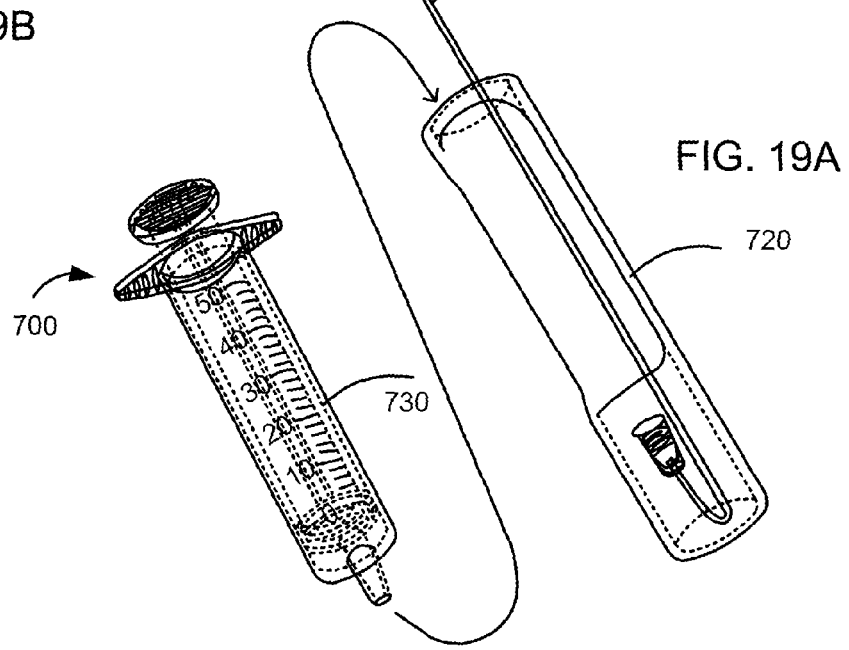
FIG. 19B
FIG. 19A

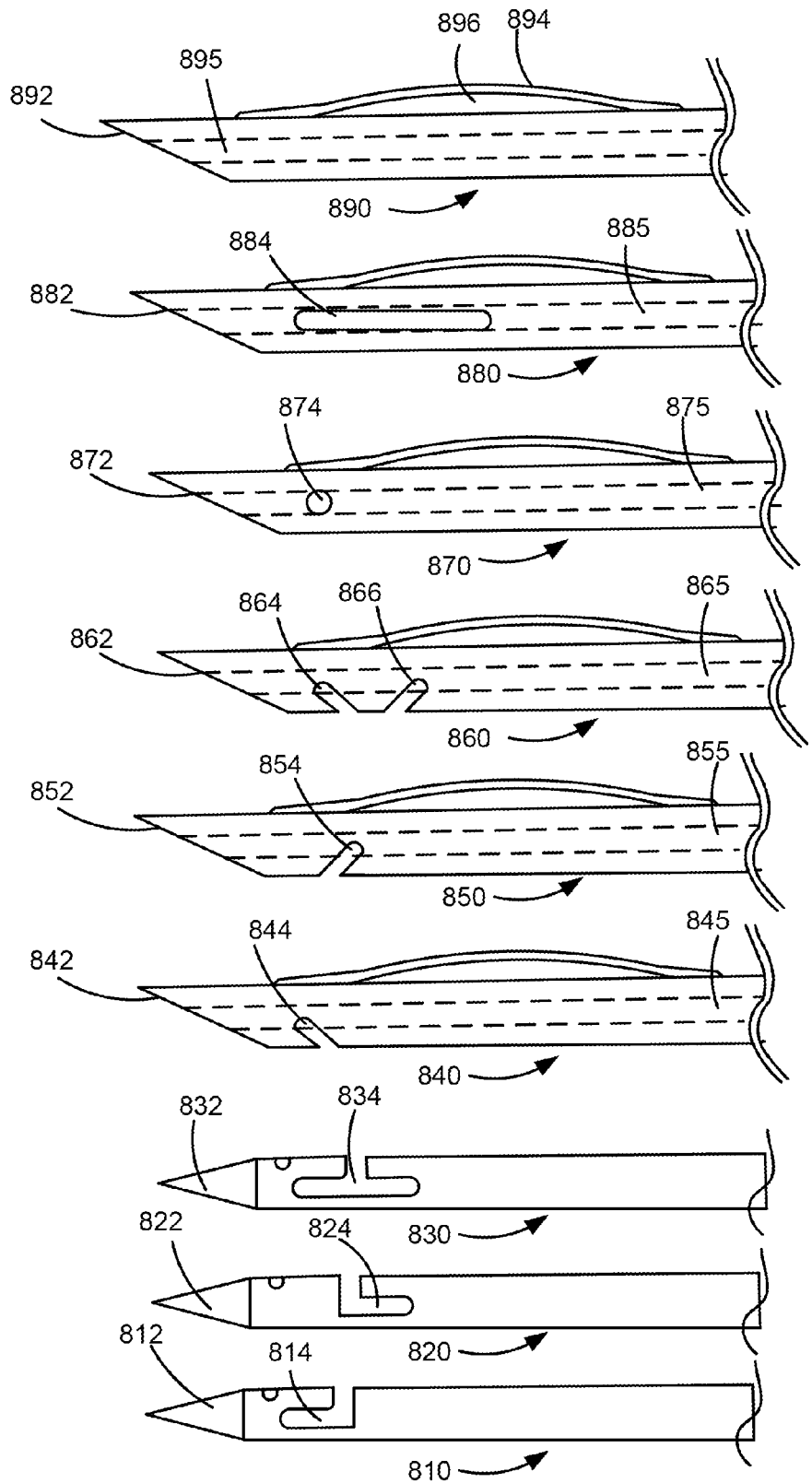

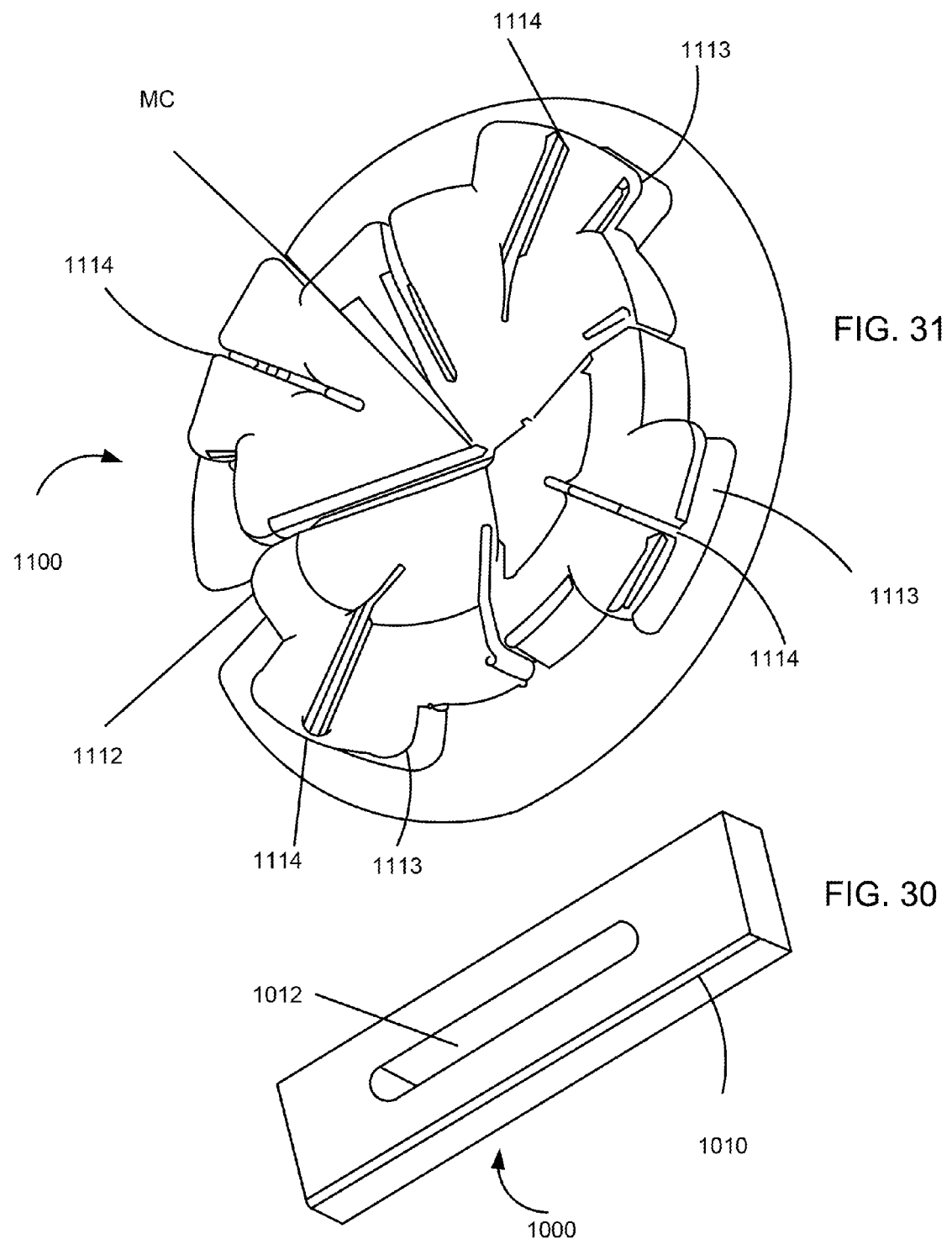

BODILY IMPLANTS AND METHODS OF ADJUSTING THE SAME

CROSS-REFERENCE TO RELATED APPLICATION

This application is a Nonprovisional of, and claims priority to, U.S. Patent Application No. 61/368,787, filed Jul. 29, 2010, entitled "BODILY IMPLANTS AND METHODS OF ADJUSTING THE SAME", which is incorporated by reference herein in its entirety.

TECHNICAL FIELD

This disclosure relates generally to medical devices and more particularly to implants configured to provide support within a body of a patient and methods for securing such implants within the body of the patient.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Women often experience vaginal prolapses due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele (small bowel prolapse) can also occur, when the small bowel pushes through the upper wall of the vagina.

Treatments of such dysfunctions have included suturing procedures or the use of medical devices or implants for support or suspension of a portion of a body of a patient. Various devices and procedures are used to deliver and secure pelvic implants within a variety of different anatomical structures within a pelvic region. Medical devices or implants can be delivered to a pelvic region through one or more vaginal incisions, and/or through exterior incisions in the patient.

Existing implants differ in many ways including size, shape, material, number and location of straps, and in the method in which they are delivered and placed within a pelvic region. Additionally, depending on the particular condition to be treated and the medical device or implant used, pelvic floor repair can require various fixation locations within a pelvic region. For example, an implant can be secured using a number of anchors disposed at various fixation points.

It may be difficult to apply the correct tension to existing medical devices or implants during the implantation procedure. Additionally, it may be difficult to adjust the tension of existing medical devices or implants at a time after the completion of the implantation procedure. Thus, it would be beneficial to provide a medical device or implant that facilitates tensioning of the medical device or implant both during the implantation procedure and at a time after the implantation procedure.

SUMMARY

A medical device includes a support member, a tether, and a retainer. The support member is configured to be placed within a body of a patient and provide support to a portion of the body of the patient. The tether forms a loop and is coupled to the support member. The tether is configured to extend from the body of the patient when the support member is placed within the body of the patient. The retainer is configured to be coupled to the tether at a first location on the tether and at a second location on the tether different than the first location. The retainer is configured to be disposed outside of the body of the patient when the support member is placed within the body of the patient.

BRIEF DESCRIPTION OF THE DRAWINGS

FIGS. 12-16 illustrate an embodiment of an insertion tool in accordance with an embodiment of the invention.

FIGS. 17-18 illustrate an embodiment of the invention.

FIGS. 19A, 19B, and 20 illustrate another embodiment of the invention.

FIGS. 21-29 illustrate end portions of insertion tools according to embodiments of the invention.

FIGS. 30-32 illustrate retainers according to embodiments of the invention.

DETAILED DESCRIPTION

The devices and methods described herein are generally directed to medical devices or implants and the delivery and placement of such medical devices or implants within a pelvic region (also referred to herein as "pelvis") of a patient. An implant or medical device can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. A single implant or multiple implants can be used in a single procedure. In some applications, when multiple implants are used, support can be provided in desired areas and improved control of the direction of stretch or support of the implant can be achieved. Various delivery devices, delivery aids, and methods are also described for delivering and securing an implant assembly within the patient. The implants and procedures described herein may be used in a female patient or a male patient.

A medical device or implant according to an embodiment of the invention can be implanted, for example, through a vaginal incision, in a retro-pubic direction (behind the pubic bone), or in a pre-pubic direction (in front of the pubic bone). In other embodiments, a medical device or implant can be placed in the direction of other anatomical structures or tissues as desired. A procedure to deploy a pelvic implant can include vaginal incisions, such as an anterior vaginal incision. In some embodiments, a procedure may include an exterior incision.

Various embodiments of medical devices and implants are described herein. A medical device or implant can be delivered to a pelvic region of a patient using a variety of different delivery devices, only some examples of which are described herein.

Figure 1:
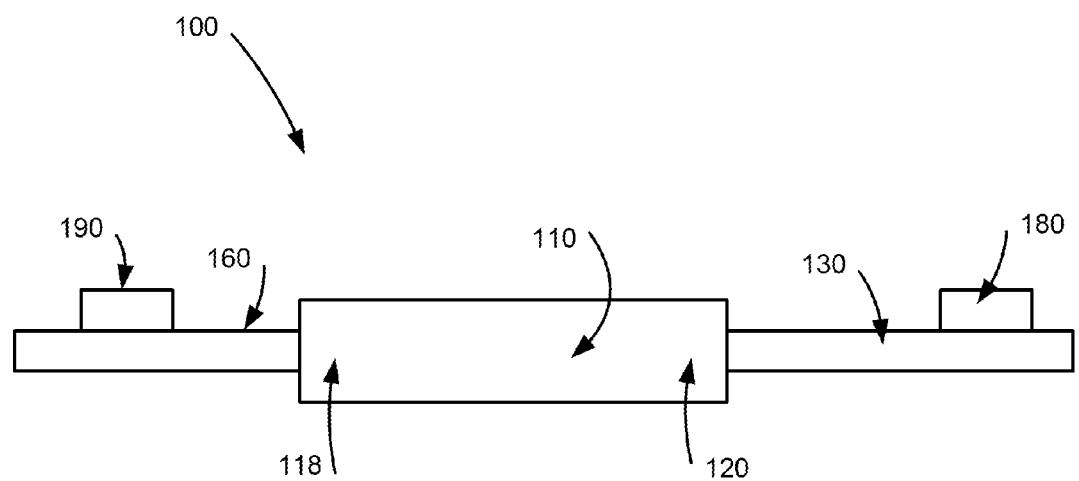
FIG. 1 is a schematic illustration of a medical device according to an embodiment of the invention.

FIG. 1 is a schematic illustration of a medical device 100 according to an embodiment. The medical device 100 includes a support member 110, a tether 130, and a retainer 180. In the illustrated embodiment, the tether 130 is coupled to an end portion 120 of the support member 110. In other embodiments, the tether 130 is coupled to other portions, such as a side portion or a medial portion of the support member 110.

In the illustrated embodiment, the medical device 100 also includes a second tether 160 and a second retainer 190. The second tether 160 is coupled to end portion 118 of the support member 110. It should be understood that the medical devices according to this invention may include any number of tethers coupled to the support member and retainers. The following discussion will focus on tether 130 and retainer 180, however it should be understood that the second tether 160 and the second retainer 190 may be structurally and functionally the same as tether 130 and retainer 180.

The support member 110 includes end portions 120 and 118 and is configured to be placed within a body of a patient to provide support to a portion of the body of the patient. For example, in some embodiments, the support member 110 of the medical device 100 is configured to be placed proximate or adjacent a bladder of a patient to provide support to the bladder of the patient. In other embodiments, the support member 110 of the implant is configured to support the urethera or bladder neck of a patient. In yet other embodiments, the support member 110 of the medical device 100 is configured to be placed adjacent another portion of the body to provide support to another portion of the body.

The first end portion 120 and the second end portion 118 are configured to be disposed within bodily tissue of the patient. In some embodiments, the first end portion 120 and the second end portion 118 are configured to be coupled to such bodily tissue to help secure the support member 110 in place within the body of the patient.

The first end portion 120 and the second end portion 118 can be of any shape or size suitable for extending between the medial portion of the support member 110 and the bodily tissue. Additionally, the medical device 100 may include additional arm members or end portions that are configured to couple to bodily tissue to help secure the medical device 100 in place within the body of the patient.

In some embodiments, the first end portion 120 and the second end portion 118 are configured to be disposed within and coupled to an obturatator membrane of the patient or other pelvic tissue of the patient. In other embodiments, the first end portion 120 and the second end portion 118 are configured to be coupled to other bodily tissue.

In some embodiments, the first end portion 120 and the second end portion 118 include tangs or tanged portions configured to help anchor the end portions 120 and 118 within the bodily tissue of the patient. The terms "tanged" or "tangs" as used herein mean roughened or jagged edges or areas, such as can result from cutting a woven or knit mesh material. In other embodiments, the end portions 120 and 118 include barbs, dimples and/or other protrusions configured to engage the bodily tissue of the patient to help retain the medical device 100 in place within the body of the patient. In other embodiments, other mechanisms may be used to couple the end portions 120 and 118 to the bodily tissue.

The support member 110 can be formed of a mesh material to allow tissue in-growth to the support member 110 after implantation within the body of the patient. For example, some or all of the support member 110 can be formed with a mesh material as described in U.S. Patent Pub. 2005/0038452 A1 to Chu, the entirety of which is hereby incorporated by reference. In some embodiments, some or all of an support member 110 can be formed with the Advantage™ Mesh or the Polyform™ Synthetic Mesh material each provided by Boston Scientific Corporation.

The support member 110 can be monolithically formed or alternatively, the support member 110 can be formed with multiple different materials and/or can include multiple different components or portions coupled together. In some embodiments, the support member can be formed with a combination of materials including synthetic and biological materials. For example, the support member 110 can be formed with a first biocompatible material and the end portions 120 and 118 can be formed with a second biocompatible material different than the first material. In other embodiments, the support member 110 is formed with a biological material, and the end portions 120 and 118 are formed with a synthetic material. In some embodiments, the end portions 120 and 118 and the support member 110 have a different weave, pitch, texture, color, and pattern from each other.

In some embodiments, the end portions 120 and 118 and the support member 110 can be coupled in an abutting relationship, an overlapping relationship, or can be bridged. The end portions 120 and 118 can be coupled to the support member 110 by, for example, heat bonding, gluing, using fasteners, and/or sewing. In some embodiments, an arm member can include a heat seal along its length or a portion of its length to help prevent or reduce stretching of the arm member.

Tether 130 is coupled to the support member 110 proximate end portion 120 of the support member 110. In some embodiments, the tether 130 is removably coupled to the support member 110. In such embodiments, the tether 130 may be removed from the support member 110 without damaging the support member 110. In some embodiments, the tether 130 is slideably coupled to the support member 110.

For example, in some embodiments, the tether 130 forms a loop and is threaded through the support member 110 (such as through an opening defined by the support member 110) such that the tether 130 is slideable or movable through the support member 110. In such an embodiment, a portion of the loop formed by the tether 130 may be cut or severed and the tether 130 may be removed from the support member 110 (such as by pulling the tether 130 in a direction away from the support member 110). In other embodiments, the tether 130 is removably coupled to the support member 110 using another type of connection, such as a tie or other releasable coupling. In some embodiments, the tether does not form a loop.

In further embodiments, the tether 130 is fixedly coupled to the support member 110. For example, in some such embodiments, an adhesive or weld is used to couple the tether 130 to the support member 110. In yet further embodiments, the support member 110 and the tether 130 are unitarily or monolithically formed. In other words, the support member 110 and the tether 130 are formed of the same piece of material.

The second tether 160 may be coupled to the second end portion 118 of the support member 110 using the same types of techniques as described with respect to the first tether 130 and the first end portion 120.

In some embodiments, the tethers 130 and 160 are sutures. In some embodiments, the first tether 130 and the second tether 160 are formed of a non-resorbable suture material. For example, in some embodiments, the first tether 130 and the second tether 160 are formed of a permanent suture material, such as polypropylene. In some embodiments, the tethers 130 and 160 have a small or narrow profile.

The retainer 180 is configured to be coupled to the tether 130. Specifically, the retainer 180 is configured to be coupled to the tether 130 at a first location on the tether 130 and a second location on the tether 130. The first location being different than the second location.

In some embodiments, the retainer 180 is movably coupled to the tether 130 or may be coupled to the tether 130 and be configured to move along the tether 130. For example, in some embodiments, the tether 130 is wound around the retainer 180. In other embodiments, the retainer 180 is slidably coupled to the tether 130. For example, the retainer 180 may define an opening that is configured to slideably receive the tether 130.

As described in greater detail below, the retainer 180 is configured to be coupled to the tether 130 such that when the tether 130 extends from the body of the patient, the retainer 180 may be coupled to the tether 130 at a location of the tether 130 that is disposed outside of the body of the patient when the support member 110 is disposed within the body. The retainer 180 is also configured to engage the body of the patient such that the tether 130 is prevented from retracting into the body of the patient. Thus, the retainer 180 is coupled to the location of the tether 130 and such that the portion (or the location) of the tether 130 to which the retainer 180 is coupled remains outside of the body of the patient.

The second retainer 190 may be structurally and functional equivalent to the retainer 180.

The medical device 100 may be placed within the body of a patient using a number of different methods. In some embodiments, the medical device 100 may be placed within the body of the patient by making a single vaginal incision and two exit incisions. The medical device 100 may be placed using an inside-out procedure (i.e., passing the medical device 100 through a vaginal incision and pushing the medical device 100 to a location within the body of the patient) or an outside-in procedure (i.e., passing an insertion tool through a skin incision and then through a vaginal incision, coupling the medical device to the insertion tool proximate the vaginal incision, and pulling the medical device 100 to a location within the body of the patient by withdrawing the insertion tool back through the skin incision).

For example, in one embodiment, the medical device 100 is placed or implanted within the body of a patient by making an incision in an anterior wall of the vagina of the patient. Tether 130 is then coupled to an insertion tool. Any number of types of insertion tools may be used. For example, an Obtryx® device as sold by Boston Scientific Corporation or a Lynx® device as sold by Boston Scientific may be used. In other embodiments, other insertion tools are used. For example, an insertion tool with a slot configured to receive the tether 130 may be used. In one embodiment, the insertion tool includes an "L" shaped slot and has a diameter of about 0.125 inches (3.18 mm). In some embodiments, a general or spinal anesthetic may be used during the placement procedure.

In one embodiment, the insertion tool is coupled to the tether 130 and the end portion 120 of the support member 110 is passed through the vaginal incision to a location within the body of the patient. The insertion tool then passes through a skin incision, thereby passing the tether 130 through the skin incision. The insertion tool may then be removed from the tether 130, retracted from the body of the patient, and associated with tether 160. In another embodiment, the tether 160 is associated with another insertion tool. The end portion 118 may then be passed through the vaginal incision and the end portion 118 may be pushed or pulled to a location within the body of the patient. The insertion tool may then be passed through a second skin incision, thereby passing the tether 160 through the second skin incision. The insertion tool may then be removed from the tether 160.

The tethers 130 and 160 may then be moved (for example, by pulling on the tethers 130 and 160 in directions away from the skin incisions) to appropriately place and tension the support member 110 within the body of the patient. For example, in one embodiment, the support member 110 is placed and tensioned below a portion of the bladder of the patient. In other embodiments, the support member 110 is disposed at a different location within the body of the patient.

Once the support member 110 is appropriately placed and tensioned within the body of the patient, the retainers 180 and 190 may be coupled to the tethers 130 and 160, respectively. The retainers 180 and 190 are coupled to the tethers 130 and 160 such that the position and tension of the support member 110 within the body of the patient is retained. Specifically, for example, retainer 180 is coupled to tether 130 at a location of tether 130 and is of a size sufficient that it does not enter the body of the patient through the skin incision through which tether 130 exits the body of the patient. Accordingly, the retainer 180 is configured to engage the skin or body of the patient surrounding the skin incision through which tether 130 exits the body of the patient to help prevent tether 130 from retracting back into the body of the patient. Thus, the placement and tension of the support member 110 within the body of the patient is retained.

The retainer 180 is removably coupled to the tether 130 such that at a time during or after the placement procedure the placement or tension of the support member 110 within the body of the patient may be adjusted. Specifically, the retainer 180 may be decoupled from the tether 130. The tether may then be moved with respect to the body of the patient (to provide more or less tension to the support member 110 or effectively lengthen or shorten the length of the medical device 100 within the body of the patient). The retainer 180 may then be coupled to the tether 130 at a second location to retain the adjusted position or tension of the support member 110.

In some embodiments, the retainer 180 may be moved and recoupled to the tether 130 for several hours or days after the procedure to place the medical device 100 within the body of the patient. Thus, the position and tension of the medical device 100 within the body of the patent may be observed and adjusted after the procedure. In some embodiments, the tethers 130 and 160 may remain coupled to the end portions 120 and 118 for a few days after the procedure to allow for further adjusting and tensioning of the support member 110.

Once the support member 110 is appropriately placed and tensioned, the tethers 130 and 160 and the retainers 180 and 190 may be removed from the support member 110. Specifically, the tethers 130 and 160 may be removed from the end portions 120 and 118 of the support member 100. In some embodiments, the tethers 130 and 160 may be removed from the end portions 120 and 118 by cutting a portion of each of the tethers 130 and 160 that is disposed outside of the body of the patient and pulling the tethers 130 and 160 in directions away from the body of the patient.

Figure 2:
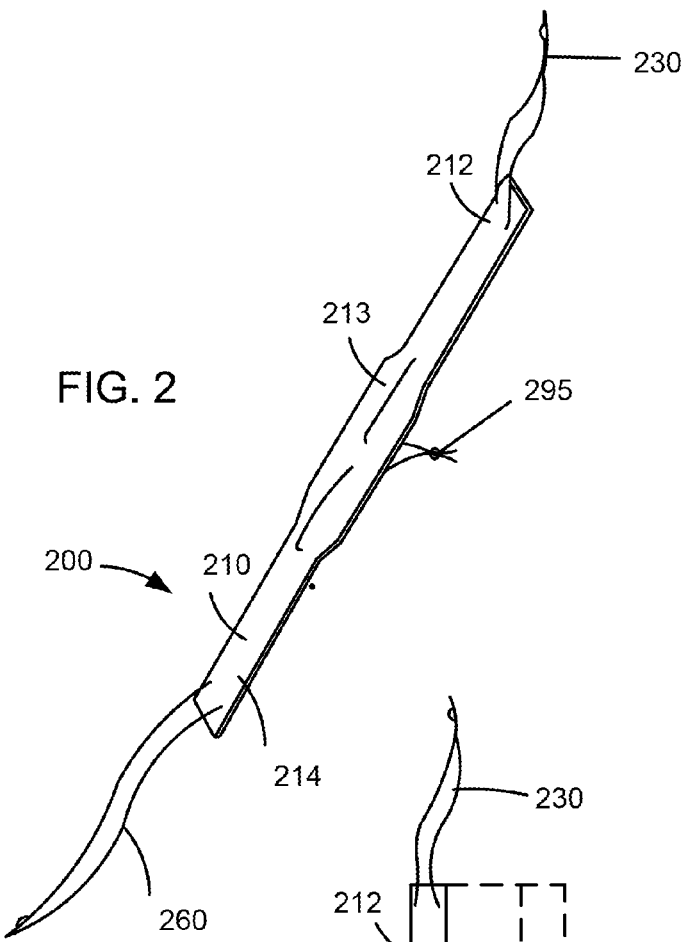
FIG. 2 is a perspective view of a portion of a medical device according to an embodiment of the invention.
Figure 3:
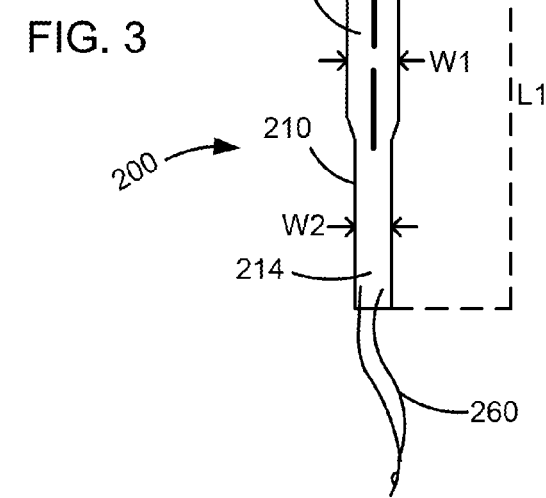
FIG. 3 is a top view of the portion of the medical device of FIG. 2.
Figure 4:
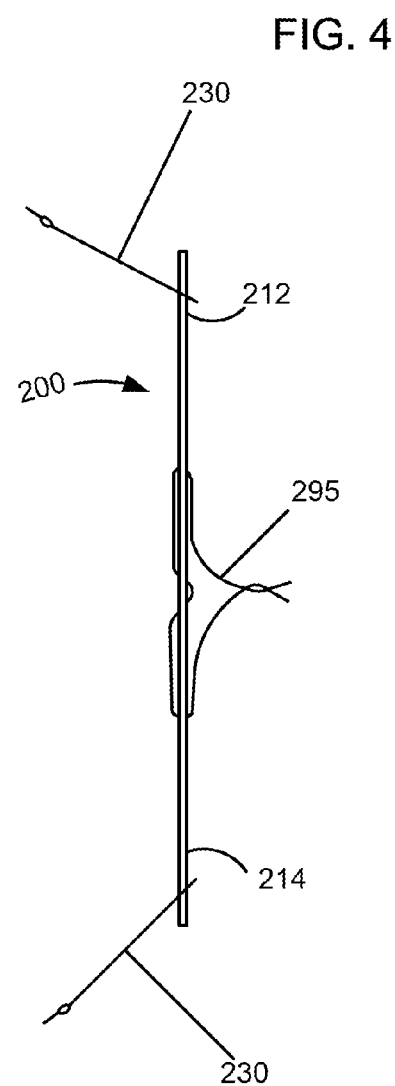
FIG. 4 is a side view of the portion of the medical device of FIG. 2.
Figure 5:
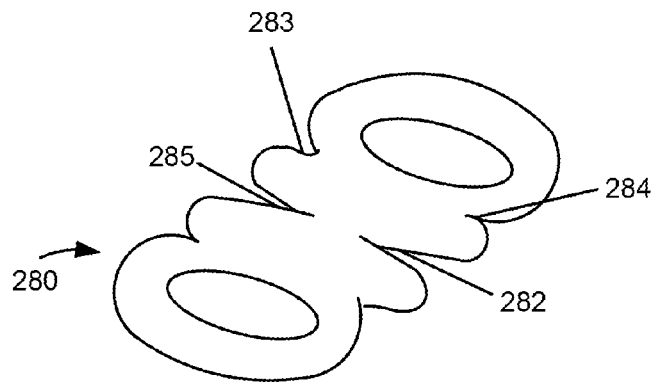
FIG. 5 is a perspective view of a retainer according to an embodiment of the invention.
Figure 8:
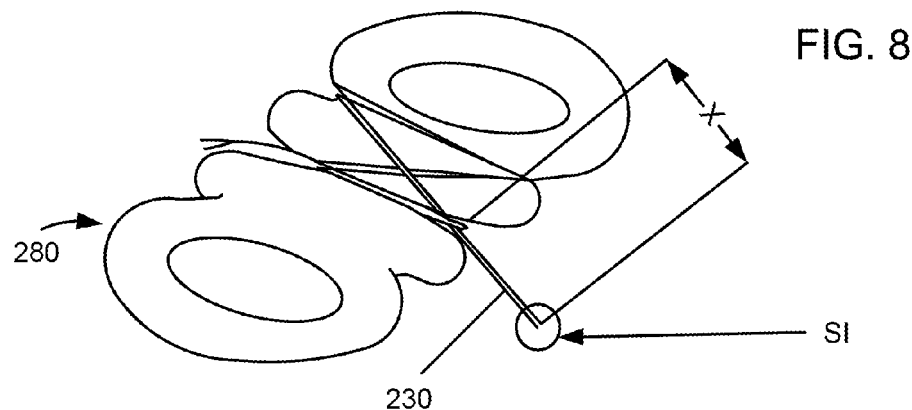
FIG. 8 is a perspective view of the retainer of FIG. 5 coupled to a tether.
Figure 7:
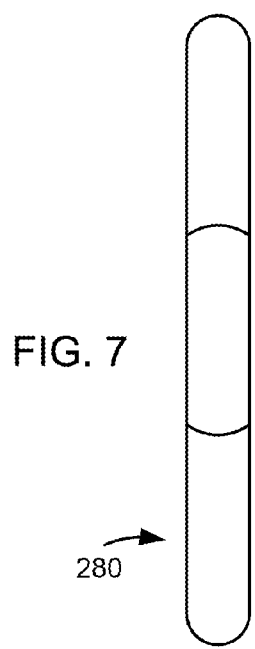
FIG. 7 is a side view of the retainer of FIG. 5.
Figure 6:
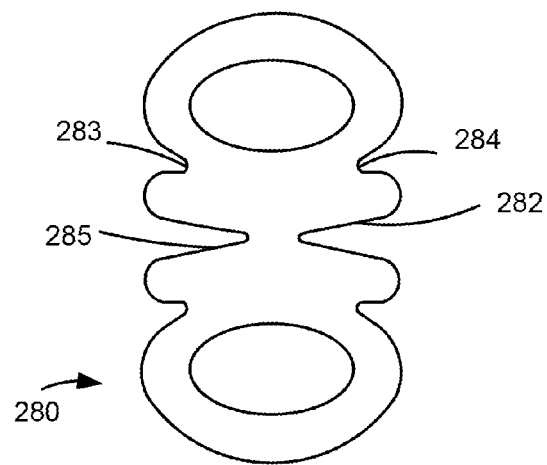
FIG. 6 is a top view of the retainer of FIG. 5

FIGS. 2-8 illustrate a medical device 200 according to an embodiment. FIGS. 2-4 illustrate a support member 210 and tethers 230 and 260 of an embodiment. FIGS. 5-7 illustrate a retainer 280 according to an embodiment. FIG. 8 is a perspective view of the tether 230 coupled to the retainer 280.

As illustrated in FIGS. 2-4, the medical device 200 includes a support member 210, a first tether 230 coupled to end portion 212 of the support member 210, and a second tether 260 coupled to end portion 214 of the support member 210. The medical device 200 also includes a third tether 295 coupled to a medial portion of the support member 210. The medical device 200 also includes a retainer 280 that is configured to be coupled to tether 230 (one of which is illustrated in FIGS. 5-7) and another retainer that is configured to be coupled to tether 260.

The support member 210 may composed of any implantable material and may be of any shape. In some embodiments, the support member 210 is formed of a synthetic material. In other embodiments, the support member 210 is formed of a biologic material. In further embodiments, the support member 210 is formed of a combination of a synthetic material and a biologic material.

In the illustrated embodiment, the support member 210 has a generally rectangular shape and includes a medial portion 213 that has a width that is greater than the width of the end portions 212 and 214. Specifically, in one embodiment for a male patient, the support member 210 has a total length L1 of about 160 mm and each end portion 212 and 214 have a length L2 of about 30-60 mm. In another embodiment for a female patient, the support member 210 has a total length L1 of about 100 mm. In other embodiments, the support member 210 has a total length greater or less than 160 mm (for a male patient) and a total length greater or less than 100 mm (for a female patient). In other embodiments, the end portions have a length greater or less than 30 mm. The width W1 of the medial portion 213 of the support member 212 may be about 12 mm and the width W2 of the end portions 212 and 214 may be about 10 mm. In other embodiments, the width of the medial portion is greater or less than 12 mm.

In some embodiments, the support member 210 includes retention members or portions. In some embodiments, the retention members or portions are configured to couple to bodily tissue, such as pelvic tissue, to help secure the support member 210 in place within the body of the patient. In some such embodiments, the retention member or portions are sufficient to retain the support member 210 in place within the body and the tethers 230 and 260 need not be coupled to retainers 280 to retain the tension and position of the support member 210 within the body of the patient. Tether 230 and 260 can be used to adjust retention members for several hours or days after the procedure to place the medical device 200 within the body of the patient. Thus, the position and tension of the medical device 200 within the body of the patent may be observed and adjusted after the procedure. In some embodiments, the support member 210 includes retention members or portions and the medical device includes retainers for additional support of the support member 210 within the body of the patient. For example, in some embodiments, the support member 210 includes tangs. In other embodiments, the support member 210 includes a jagged or "Christmas tree" profile to help secure the support member 210 in place within the body of the patent. In yet further embodiments, the support member includes darts or other anchor members to help secure the support member in place within the body of the patient. In some embodiments the retention member only allows only one way adjustment. In some embodiments the darts (without barbs) do not secure but are used to as leading edges.

In some embodiments, the support member 210 is devoid of retention members. In some embodiments, one end portion of the support member 210 includes retention member and the other end portion is devoid of retention members. In some such embodiments, only one end portion of the support member 210 is adjusted. Additionally, in some such embodiments, the tether 295 is biased or located toward the end portion that does not include retention members.

In some embodiments, the support member 210 is formed of a material that is configured to prevent stretch under tension. In some embodiments, that support member 210 is configured such that it is prevented from unraveling. For example, in some embodiments, a mesh material (such as the Advantage® mesh as sold by Boston Scientific Corporation) that forms the support member may be detanged to help prevent unraveling. In some embodiments, only a portion of the support member 210 is detanged. In other embodiments, the entire support member 210 is detanged.

In the illustrated embodiment, the tethers 230, 260 and 295 form loops and are slideably coupled to the support member 210. Specifically, the tethers 230, 260 and 295 are threaded through portions of the support member 210. Tethers 230 and 260 are coupled to the end portions 212 and 214 of the support member 210, respectively, and are of a length sufficient to extend from the body (for example, through the skin incisions) of the patient when the support member 210 is placed within the body. In some embodiments, the tether 295 is also of a length sufficient to extend from the body of the patient when the support member 210 is placed within a body of the patient (for example, through the vaginal incision).

The loops of the tethers 230, 260, and 295 may be formed by knotting or crimping two ends of the tethers together. In some embodiments, the crimp may include a coupling mechanism configured to removably couple the tether to an insertion tool. For example, the crimp may include a hook or a snap configured to engage the insertion tool. In some embodiments, the tethers 230, 260, and 295 are sutures. For example, the tethers 230, 260, and 295 can be formed of an absorbable suture material or a non-absorbable suture material. In some embodiments, the tethers 230, 260, and 295 are of a minimal profile so as to minimize the size of the exit site and to minimize the injury to the surrounding bodily tissue.

The tethers 230, 260, and 295 may be coupled to the support member 210 using any known method. For example, the tethers 230, 260, and 295 may be passed through or threaded through a portion of the support member 210. In some embodiments, the tethers 230, 260, and 295 weave through a portion of the support member 210. For example, as illustrated in FIG. 2, tethers 230 and 260 weave through the support member 210 once. Additionally, as illustrated in FIG. 2, tether 295 weaves through the support member 210 multiple times.

In some embodiments, that tethers 230 and 260 are configured to be coupled to or associated to an insertion tool or delivery device such as the Obtryx Halo™, the Obtryx Curve™, and the Lynx® delivery devices as sold by Boston Scientific Corporation to facilitate the placement of the implant 200 into the body of the patient. In some embodiments, the delivery device includes an "L" shaped slot that is configured to be associated with the tethers 230 and 260. In some embodiments the delivery device includes a needle that has a diameter of about 0.125 inches (3.18 mm). In some embodiments, as will be described in detail below, a general or spinal anesthetic is used when the implant 200 is placed within the body of the patient.

In some embodiments, the tethers 230, 260, and 295 are color coded. In some embodiments, the tether 295 is biased or located toward one end portion of the support member. In some such embodiments, only one of the tethers is used to adjust the position or tension of the support member 210. In some embodiments, the medical device includes a fourth tether coupled to the medial portion of the support member. Thus, more precise adjustments may be made to the lengths of individual portions of the support member. Also, in some such embodiments, the tethers may be color coded. For example, tether 230 and 295 may be of a first color and tether 260 and the fourth tether may be of a second different color.

FIGS. 5-8 illustrate a retention member 280 according to an embodiment of the invention. It should be understood that while only one retention member 280 is illustrated and described in detail, the medical device may include more than one retention member. The retention member 280 is a spooler and is configured to be removably coupled to the tether 230 such that at any time during or after the placement procedure the placement or tension of the support member 110 within the body of the patient may be adjusted. As described in more detail below, the retention member 280 may be decoupled from the tether 230. The tether 230 may then be moved with respect to the body of the patient (to provide more or less tension to the support member 210 or to effectively lengthen or shorten the length of the medical device 200 within the body of the patient). The retainer 280 may then be coupled to the tether 230 at a second location to retain the adjusted position or tension of the support member 210.

In some embodiments, the retainer 280 may be moved and recoupled to the tether 230 after several hours or days after the procedure to place the medical device 200 within the body of the patient. Thus, the position and tension of the medical device 200 within the body of the patent may be observed and adjusted for a period of time after the procedure. In some embodiments, the tethers 230 may remain coupled to the support member 210 for a few days after the procedure to allow for further adjusting and tensioning of the support member 210. Once the support member 210 is appropriately placed and tensioned, the tethers 230 and the retainers 280 may be removed from the support member 210. In some embodiments, only one of the retainers is removed from and recoupled to the appropriate tether to adjust the tension and position of the support member 210.

The retainer 280 is configured such that the tether 230 may be wound around the retainer 280 (as best illustrated in FIG. 8). In the illustrated embodiment, the retainer 280 is generally flat and defines four (4) slots 282, 283, 284, and 285. In some embodiments, the slots 282, 283, 284, and 285 are of different sizes. In some embodiments, the slots 282, 283, 284, and 285 are of the same or similar sizes. In the illustrated embodiment, the distance between slot 282 and slot 285 is smaller than the distance between slot 283 and slot 284. Accordingly, the tether 230 may be wound around the retainer 280, within the slots 282, 283, 284, and 285, to couple the retainer 280 to the tether 230 (at a location of the tether 230). The tether 230 may be unwound from the retainer 280 to remove or decouple the retainer 280 from the tether 230.

In other embodiments, the retainer includes more than four (4) slots for receiving the tether. In further embodiments, the retainer includes less than four (4) slots for receiving the tether.

In some embodiments, rather than coupling to retainers, the tethers 230 and 260 are sutured to the skin of the patient to retain the support member 210 in place within the body of the patient.

Figure 9:
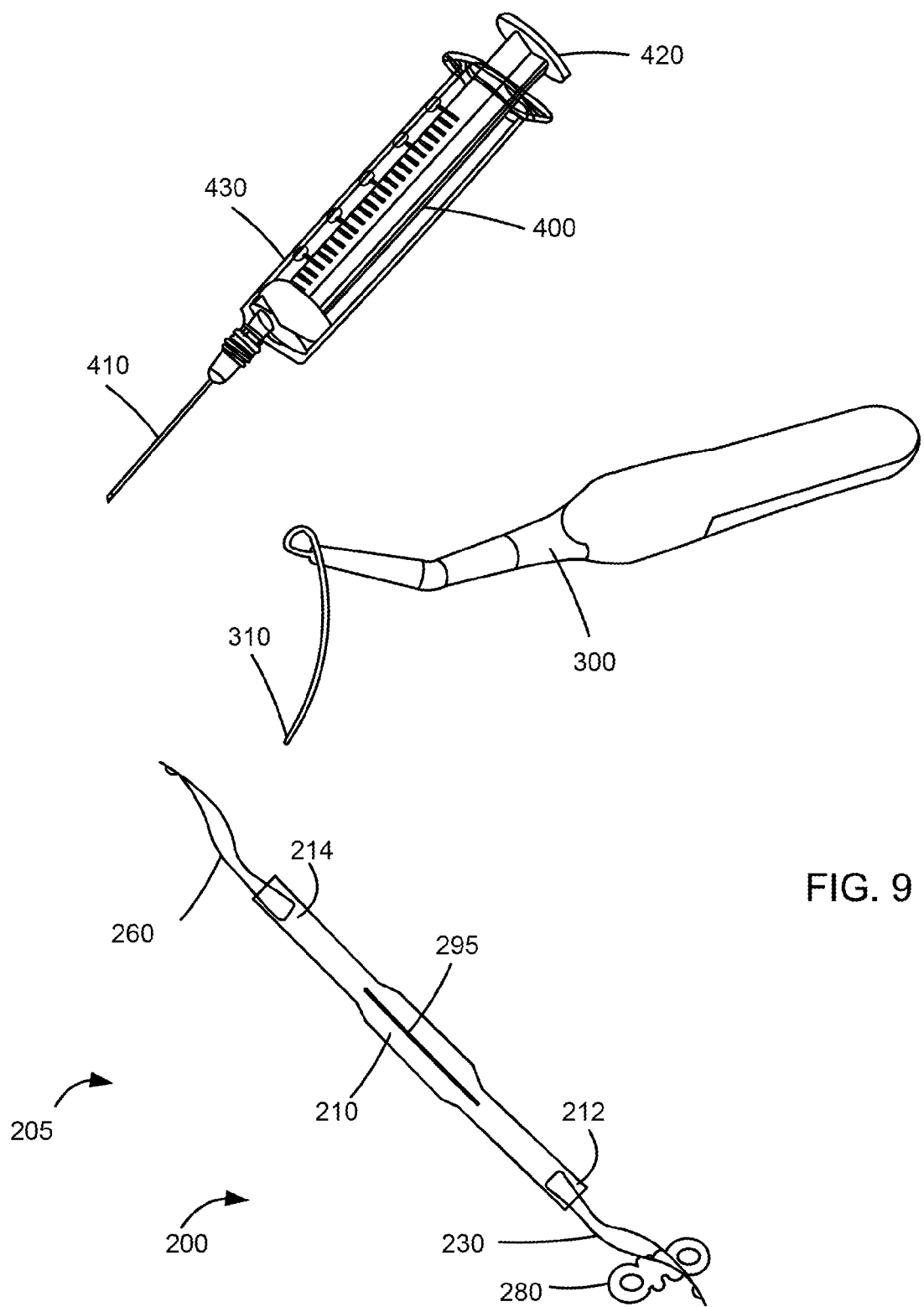
FIG. 9 is a perspective view of a kit according to an embodiment of the invention.

FIG. 9 illustrates a kit 205 according to an embodiment of the invention. The kit 205 includes medical device 200, an insertion tool or delivery device 300, and an injection device or syringe 400. The medical device 200, includes the support member 210, the tethers 230, 260, and 295, and retainers 280 (only one is illustrated though it should be understood that in some embodiments, the medical device 200 includes two retainers).

The injection device 400 is configured to inject material into the body of that patient during the procedure to place the medical device 200 within the body of the patient. For example, in some embodiments, the injection device 400 is configured to inject an anesthetic into the patient. In some embodiments, an anesthetic such as lidocaine, lidocaine with epinephrine, bupivacaine, bupivacaine with epinephrine, or mepivacaine may be used. In other embodiments, the injection device 400 is configured to inject a medication into the body of the patient. In the illustrated embodiment, the injection device includes a needle 410, a plunger 420, and a barrel 430. In some embodiments, the injection device 400 includes a 21 gauge hypodermic needle.

In some embodiments, the kit includes two insertion tools or delivery devices 300. For example, in one embodiment, the kit includes a "right" insertion tool (for delivering a portion of the medical device 200 to the right side of the patient) and a "left" insertion tool (for delivering a portion of the medical device 200 to the left side of the patient). In such an embodiment, one of the "right" insertion tool and the "left" insertion tool would have a needle or body that curves in a clockwise direction and the other would have a needle or body that curves in a counter-clockwise direction. In some embodiments where two insertion tools are provided, a single cystoscopy can be performed to detect inadvertent punctures of the urethra or bladder when both insertion tools are disposed within the body of the patient.

In the illustrated embodiment, the insertion tool or delivery device 300 is configured to place the medical device 200 within the body of the patient. For example, in some embodiments, that insertion tool 300 is configured extend through the obturator membrane or muscles of the patient to extend the medical device 200 through the obturator membranes or muscles. In some embodiments, the insertion tool or delivery device 300 is the Obtryx Halo™ device as sold by Boston Scientific Corporation.

In some embodiments, the needle of the insertion tool is covered or includes an outer sleeve. The space between the needle and the sleeve may be used for the injection of medication or anesthesia into the body of the patient near the passageway of the needle.

In some embodiments, the outer diameter of the insertion device is sufficiently small such that it is less invasive than other insertion devices and allows the use of only a local anesthetic when performing the insertion procedure. In some embodiments, the insertion tool or delivery device 300 has an outer diameter of about 16 gauge. In some embodiments, the outer diameter of the insertion tool is about 0.06 inches (1.5 mm). In other embodiments, that outer diameter of the insertion tool is larger or smaller than 16 gauge. Accordingly, in some embodiments, the insertion procedure may take place in an office setting rather than in a surgical room setting.

In some embodiments, the insertion tool or delivery device 300 includes a slot for associating a tether with the insertion tool or delivery device 300. In the illustrated embodiment, the slot is disposed at a distal end portion 310 of the insertion tool 300. In some embodiments, the insertion tool 300 includes an L shaped slot. In other embodiments, the insertion tool 300 includes a T shaped slot. In some embodiments, the insertion tool 300 includes a distal end portion that is sharp. Accordingly, the insertion tool 300, in some embodiments, includes a conical or bevel cut distal end portion.

To place the medical device into the body of the patient, a local anesthetic may be provided to the patient via the injection device 400. The medical device 200 may then be placed within the body of the patient using an inside-out approach or an outside-in approach. The methods of delivery can also include transobturator, retro-pubic, supra-pubic, and pre-pubic approaches.

Using an inside-out approach, the medical device 200 is placed within the body of the patient by making a single vaginal incision and two exit incisions. Specifically, in one embodiment, the medial device 200 is placed or implanted within the body of a patient by making an incision in an anterior wall of the vagina of the patient. End portion 212 is then coupled via the tether 230 to the insertion tool 300 and the end portion 212 of the support member 210 is passed through the vaginal incision to a location within the body of the patient. The insertion tool 300 then passes through a skin incision, thereby passing the tether 230 through the skin incision. The insertion tool 300 may then be removed from the tether 230 and removed from the body of the patient by withdrawing the tool though the vaginal incision. In some embodiments, that insertion tool 300 is used to pass the end portion 212 of the support member 210 through obturator membranes or muscles of the patient. In other embodiments, the insertion tool 300 is used to pass the end portion 212 of the support member 210 through other pelvic tissue.

The same procedure can be used to place the end portion 214 of the support member 210 within the body of the patient. For example, in some embodiments, the end portion 214 is placed on the opposite side of the patient than the side in which end portion 212 is placed.

Using an outside-in approach, the insertion tool 300 can be inserted into the body of the patient at the skin incision. The insertion tool 300 can then be passed through the body of the patient to the midline or vaginal incision. End portion 212 of the support member 210 of the medical device 200 can then be associated to the insertion tool 300 (i.e., by coupling or associating the tether 230 with insertion tool 300). The insertion tool 300 can then be withdrawn from the body of the patient. Thereby pulling the medical device 200 into the body of the patient through the vaginal or midline incision. Once the tether 230 extends from the skin incision, the tether 230 can be removed from the insertion tool 300. In some embodiments, a thimble may be worn by the physician to provide protection from the end portion of the insertion tool 300.

The same procedure can be used to place the end portion 214 of the support member 210 within the body of the patient. For example, in some embodiments, the end portion 214 is placed on the opposite side of the patient than the side in which end portion 212 is placed.

Figure 10:
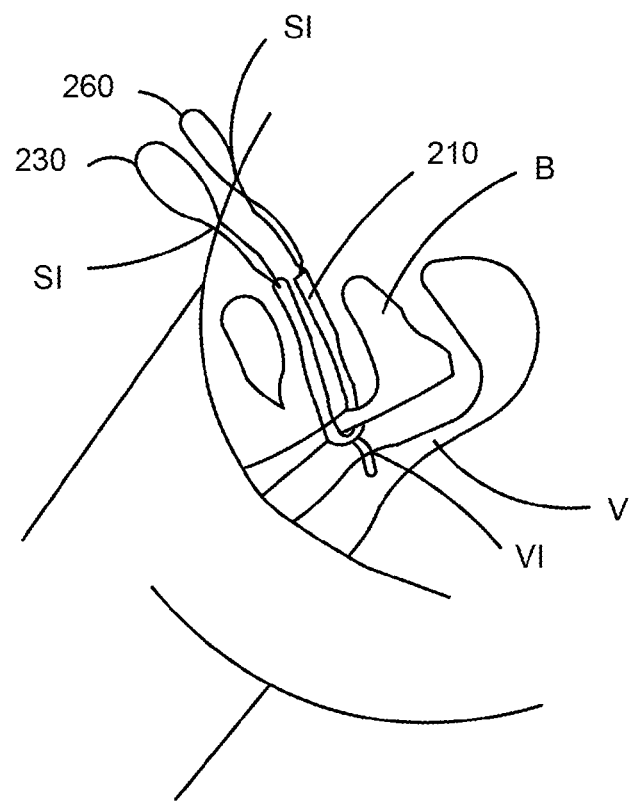
FIGS. 10, 10A, 11, and 11A are schematic illustrations of the medical device disposed within a body of a patient.
Figure 10A:
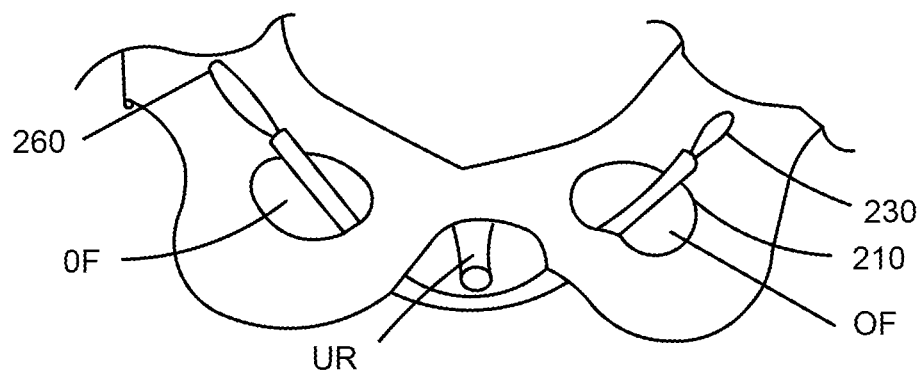

Once both tethers 230 and 260 extend from the skin incisions SI as illustrated in FIG. 10, the tethers 230 and 260 may then be moved (for example, by pulling on the tethers in directions away from the skin incisions) to appropriately place and tension the support member 210 within the body of the patient. For example, in one embodiment, the support member 210 is placed and tensioned between a portion of the bladder B and the vagina V of the patient. In one embodiment, as illustrated in FIG. 10A, the support member 210 is placed below the urethera UR of a patient and extends through the obturator foramens OF of the patient.

Once the support member 210 is placed and tensioned within the body of the patient, the retainers 280 may be coupled to tethers 230 and 260, respectively, to retain the position and tension of the support member 210 within the body of the patient. For example, the retainers 280 are each coupled to a location of the tethers 230 and 260 that is disposed outside of the body of the patient. The retainers 280 engage the skin or body of the patient that surrounds the skin incisions SI to retain the tension and portion of the support member 210 within the body of the patient.

In one embodiment, the tethers 230 and 260 are wrapped around the retainers 280 to couple the retainers 280 to the tethers 230 and 260. For example, with respect to retainer 280 and tether 230 (as illustrated in FIG. 8), the tether 230 may be wrapped around the retainer 280 as follows. A length X of the tether 230 is spaced between the retainer 280 and the skin incision SI. The retainer 280 is then held stationary and the tether 230 is wound around the retainer 280. For example, the tether 230 may be wrapped from slot 282, to slot 283, to slot 284, and to slot 285. Then to trap the end portion of the tether 230 (or to couple the tether 230 to the retainer 280), the retainer 230 is rotated such that the entire length X of the tether 230 is wrapped around the retainer 280.

In some embodiments, the retainer 280 engages the skin or portion of the body surrounding the skin incision SI and is prevented from twisting or turning. In some embodiments, the retainer 280 is taped to the skin or portion of the body surrounding the skin incision SI to help prevent the retainer 280 from twisting or turning.

A similar procedure may be used to a retainer to the tether 260.

The tension or position of the support member 210 within the body of the patient may be adjusted by winding more of the tethers 230 and 260 onto the retainers 280 or by unwinding some of the tethers 230 and 260 from the retainers 280. Accordingly, the retainers 280 may be coupled to different portions of the tethers 230 and 260 to adjust the tension and position of the support member 210 within the body of the patient.

In some embodiments, tether 295 is configured to extend from the vaginal or midline incision VI after the procedure to place the medical device within the body of the patient. In some embodiments, the tether 295 may be manipulated, such as by pulling tether 295 in a direction away from the body of the patient to loosen the tension of the support member 210 within the body of the patient. In such an embodiment, the retainers 280 would be removed or loosened from the tethers 230 and 260 before the tether 295 is pulled in a direction away from the body of the patient.

Accordingly, the tension or position of the support member 210 may be adjusted during or after the procedure to place the medical device within the body of the patient. For example, in some embodiments, the support member 210 may be adjusted 24 or 48 hours after the procedure to place the medical device within the body of the patient. Once the support member is readjusted, the retention members may be retaped to the body of the patient.

Figure 11:
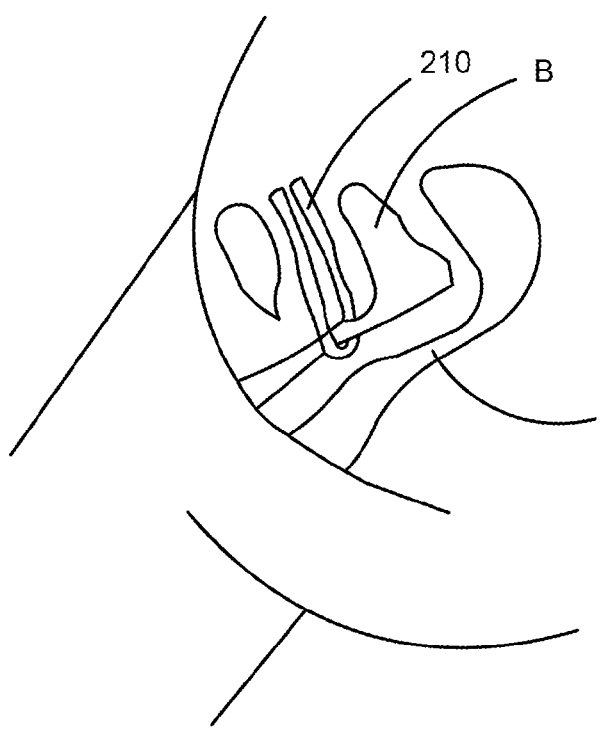
Figure 11A:
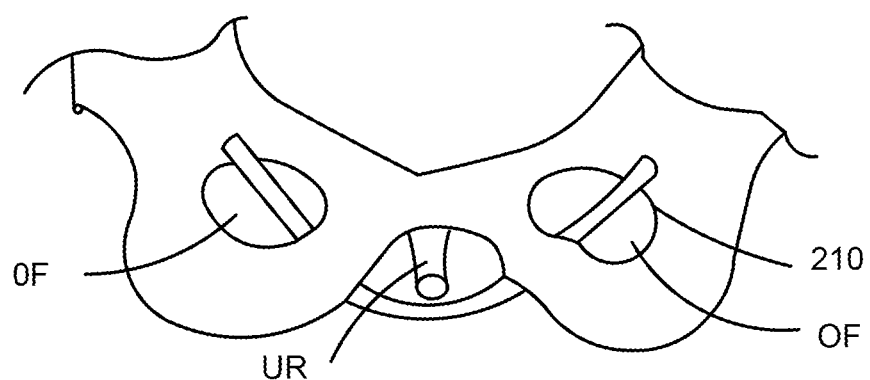

As illustrated in FIGS. 11 and 11A, in some embodiments, the tethers 230, 260, and 295 and the retainers 280 may be removed from the body of the patient. For example, once tissue in-growth stabilizes the support member 210 within the body of the patient, the tethers 230 and 260 and the retainers 280 may be removed. The tether 295 may also be removed.

In some embodiments, that tethers 230 and 260 and the retainers 280 may be removed by cutting or severing a portion of the tethers 230 and 260 (for example, on side of the loop) and pulling the tethers 230 and 260 away from the body of the patient. Thus, the tethers 230 and 260 will be released and pulled through the support member 210. Additionally, tether 295 may be removed in a similar manner (leaving only the support member 210 within the body of the patient).

In other embodiments, the tethers 230 and 260 can be cut below the level of the skin incision and the remainder of the tethers 230 and 260 remain in place within the body of the patient.

FIGS. 12-16 illustrate another embodiment of an insertion tool or delivery device 500. FIG. 16 is an expanded view of portion A of FIG. 15. The insertion tool or delivery device 500 defines a lumen 502 that extends through the insertion tool 500 (from the distal end portion 504 to the proximal end portion 506 of the insertion tool 500). The insertion tool 500 includes a luer hub 510 on the proximal end portion of the insertion tool 500. The luer hub 510 may be used to couple a syringe to the insertion tool 500. The syringe may be used to deliver anesthetic or medications to ease post-operative pain, to aid in rapid tissue in-growth, or to prevent infections. In some embodiments, the lumen 502 may be used to hydro-dissect tissue during the insertion procedure.

In the illustrated embodiment, the distal end portion 506 of the insertion tool 500 includes a T shaped slot 508 (which is configured to engage a tether of a medical device). In the illustrated embodiment, the T shaped slot 508 has a width N of about 0.2 inches (0.5 mm) and has an outer diameter of about 0.06 inches (1.5 mm).

FIGS. 17-18 illustrate an insertion tool or delivery device 600 according to another embodiment of the invention. FIG. 18 is a expanded view of portion G of FIG. 17. The insertion tool 600 includes a syringe 680 disposed in a housing 690. The insertion tool 600 includes a syringe handle 620. The physician may activate and aspirate the syringe during the insertion or removing of the insertion tool 600. For example, the physician may activate the syringe with a single hand while the other hand directs the path of the needle. The plunger of the syringe may be activated by the thumb of the physician.

In the illustrated embodiment, the needle shaft 630 is shaped to be used in a retro-pubic (inside-out) approach or a supra-pubic (outside-in) approach. In one embodiment, the needle has an outer diameter of about 16 gauge. In one embodiment, the needle shaft has an outer diameter of about 0.06 inches (1.5 mm).

The same insertion tool 600 may be used to deliver both end portions of the support member into the body of the patient. A loop in the tether 260 (which may be colored to facilitate viewing) and the needle shaft 630 may be used to perform a single cystoscopy.

In the illustrated embodiment, the tether 260 is associated with the insertion tool via an eyelet 650 defined by the insertion tool 600. In some embodiments, a single strand 261 is used to associate a looped tether to the insertion tool 600. For example, the tether may have a loop on one end and be a single strand on the other end. In some embodiments, the single strand portion 261 of the tether is removed after it exits the skin incision and the looped portion is used to couple to the retainer as described above.

In some embodiments, an eyelet threader may be used to thread the tether through the eyelet.

FIGS. 19A, 19B, and 20 illustrate another embodiment of an insertion tool 700. FIG. 19B is an expanded view of portion H of FIG. 19A. The insertion tool 700 includes a needle 710 that has a curved portion that facilitates the delivery of the medical device through an obturator of the patient. In one embodiment, the needle 710 has an outer diameter of about 16 gauge. In one embodiment, the needle 710 has an outer diameter of about 0.06 inches (1.5 mm). The needle 710 defines an eyelet 712 that is configured to receive an eyelet loop 714. The eyelet loop 714 is flexible and can be dragged along the side of or behind the needle and can be associated with the medical device. The eyelet loop 714 is configured to facilitate the association of the tethers of the medical device with the eyelet 712 defined by the needle 710.

In some embodiments, the syringe 730 is removable from the housing 720 of the delivery device 700. Thus, the medication can be refilled or exchanged.

As illustrated in FIG. 20, in some embodiments, the needle portion is formed of a single material. For example, in some embodiments, the needle portion is formed of a single piece of MP35N, Nickel-cobalt-chromium-molybdenum, high strength alloy. In other embodiments, the needle is formed of a different material, such as stainless steel. In some embodiments, the needle is formed of multiple materials. For example, in one embodiment, the distal end portion P of the needle 710 is formed of MP35N, Nickel-cobalt-chromium-molybdenum, high strength alloy and the proximal end portion R is formed of a plastic material. For example, the proximal end portion can be a plastic extension connector.

Figure 20A:
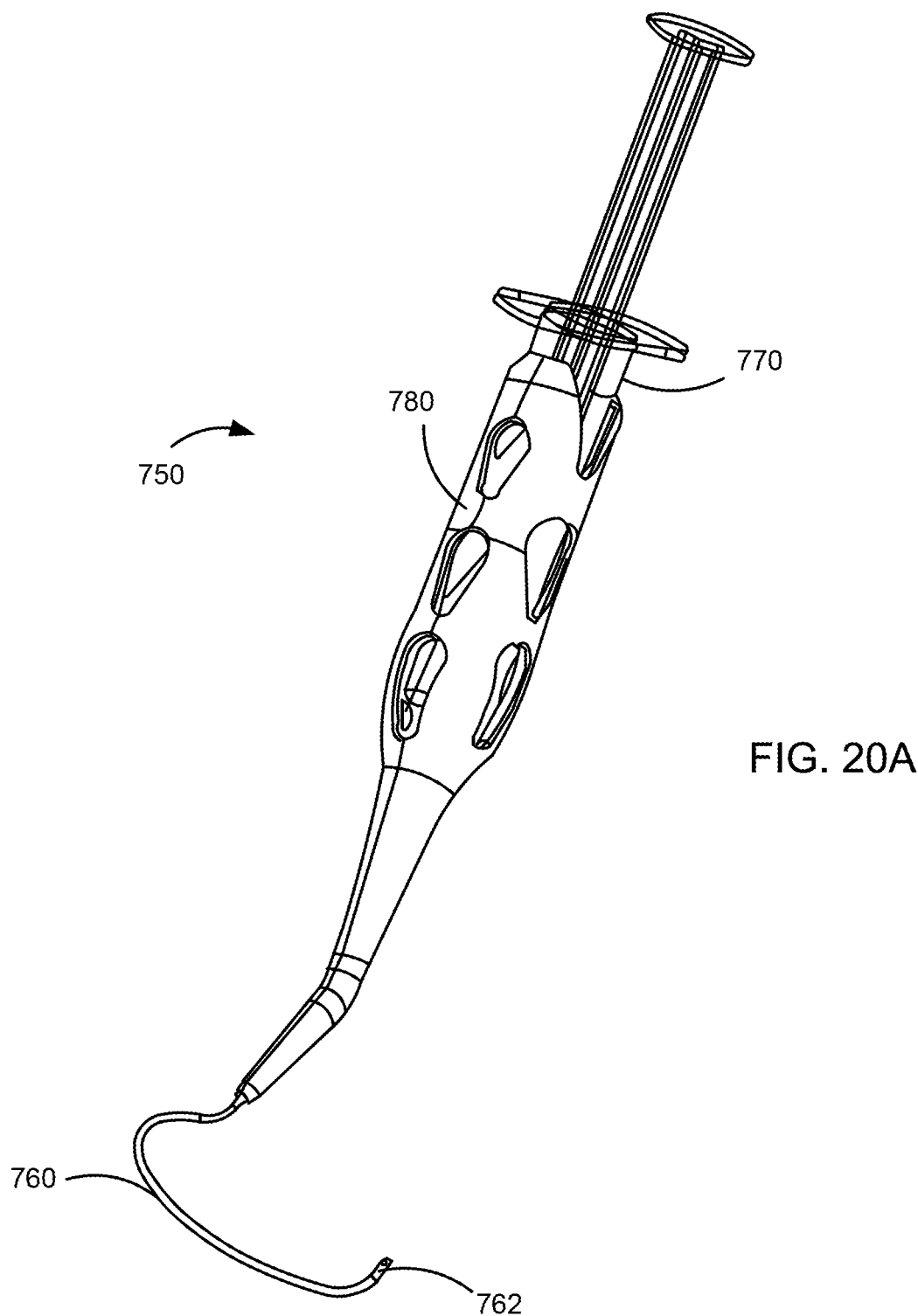
FIG. 20A illustrates another embodiment of the invention.

FIG. 20A illustrates another embodiment of an insertion tool 750. The insertion tool 750 includes a needle 760 that has a curved portion that facilitates the delivery of the medical device through an obturator of the patient. In one embodiment, the needle 760 has an outer diameter of about 16 gauge. In one embodiment, the needle 760 has an outer diameter of about 0.06 inches (1.5 mm). The needle 760 defines an eyelet 762 that is configured to be associated with the medical device.

The insertion tool 750 also includes a syringe 770. In some embodiments, the syringe 770 is removable from the housing 780 of the insertion tool 750. Thus, the medication can be refilled or exchanged.

FIGS. 21-29 illustrate distal end portions of insertion tool according to different embodiments of the invention that include different mechanisms for coupling to the tethers. As illustrated in FIG. 21, the insertion tool 810 includes a tapered end 812 and defines an L shaped slot 814. As illustrated in FIG. 22, the insertion tool 820 includes a tapered end 822 defines an L shaped slot 824 (with the long portion of the "L" closer to the proximal end of the insertion tool 820). As illustrated in FIG. 23, the insertion tool 830 includes a tapered end portion 832 and defines a T shaped slot 834. As illustrated in FIG. 24, the insertion tool 840 defines a lumen 845 that extends through a portion of the insertion tool 840. The distal end portion of the insertion tool 840 includes an angled end portion 842 and defines an angled slot 844. As illustrated in FIG. 25, the insertion tool 850 defines a lumen 855 that extends through at least a portion of the insertion tool 850. The insertion tool 850 includes an angled end portion 852 and defines an angled slot 854 (which is angled toward the proximal end portion of the insertion tool 850). As illustrated in FIG. 26, the insertion tool 860 defines a lumen 865 that extends through at least a portion of the insertion tool 860. The insertion tool 860 includes an angled end portion 862, and defines two angled slots 864 and 866. As illustrated in FIG. 27, the insertion tool 870 defines a lumen 875 that extends through at least a portion of the insertion tool 870. The insertion tool 870 includes an angled end portion 872 and defines a circular eyelet 874. As illustrated in FIG. 28, the insertion tool 880 defines a lumen 885 that extends through at least a portion of the insertion tool 880. The insertion tool 880 includes an angled end portion 882 and defines an oval or elongated eyelet 884. As illustrated in FIG. 29, the insertion tool 890 defines a lumen 895 that extends through at least a portion of the insertion tool 890. The insertion tool 890 includes an angled end portion 892 and includes a wire 894 coupled to a side portion of the insertion tool 890 to define an opening 896.

The retainer can be of any shape or size sufficient to be coupled to the tether and retain tether at a position outside of the body of the patient. In some embodiments, the retainer is configured to be coupled to the tether by tying the tether to the retainer. For example, as illustrated in FIG. 30, a retainer 1000 includes an elongate member 1010 that defines an opening 1012. Any method of coupling the tether to the retainer 1000 may be used. For example, in one embodiment, the tether is passed through the opening 1012 and the tether is then wound around the elongate member 1010. A piece of tape may then be used to couple the retainer 1000 to the skin surrounding the skin incision and prevent the retainer 1000 from twisting or rotating.

FIG. 31 illustrates a retainer 1100 according to another embodiment of the invention. The retainer 1100 defines an inlet slot 1112 and retention slots 1114. The tether may be inserted into the inlet slot to allow the middle MC of the retainer to be placed over the skin incision. The tether may then be wrapped around the retainer 1100 and secured to one of the retention slots 1114 to couple the tether to the retainer 1100. Specifically, in the illustrated embodiment, the tether may be wrapped around the retainer 1100 and between grooves 1113 defined by the retainer 1100.

Figure 32:
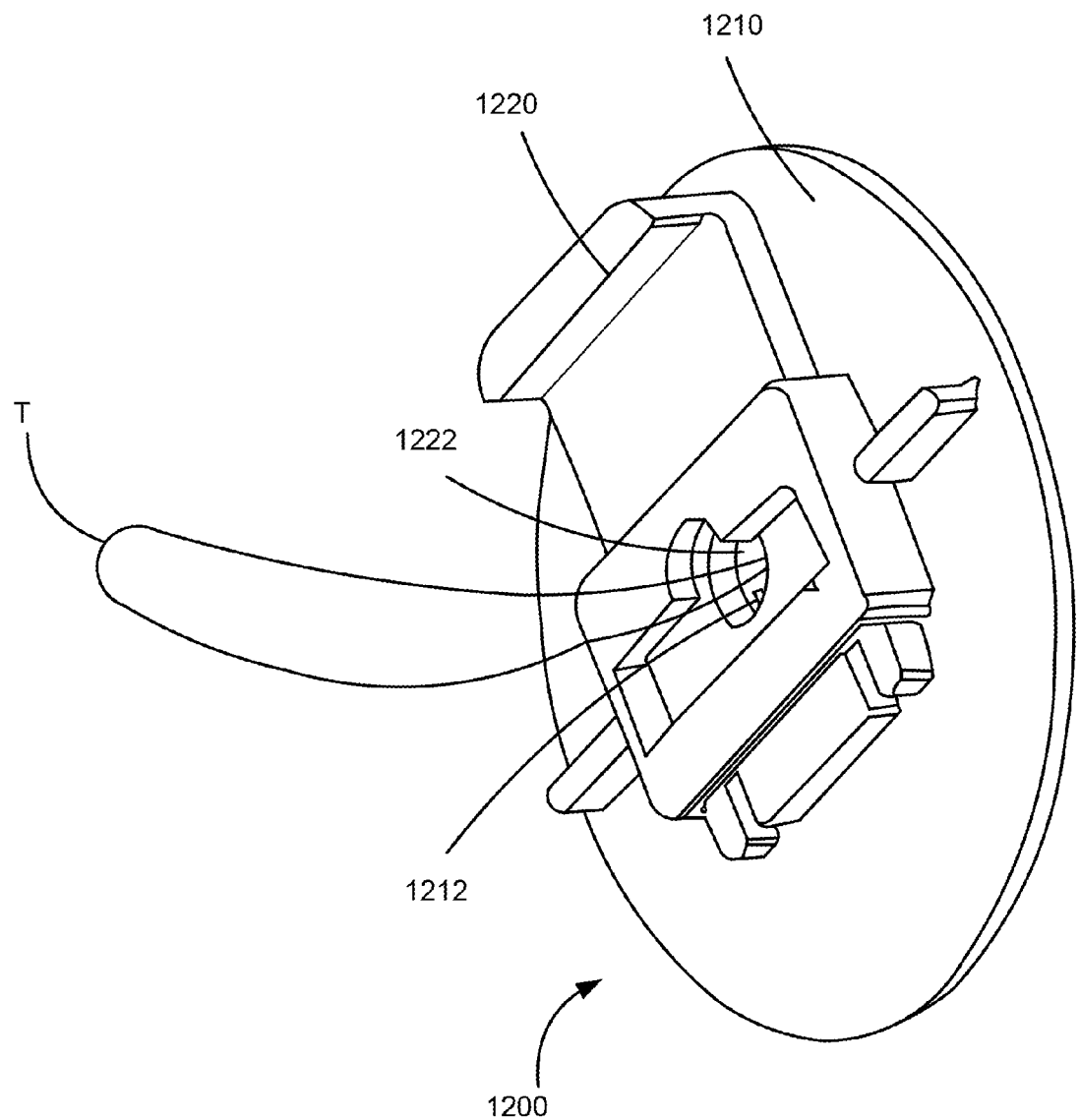

FIG. 32 illustrates a retainer 1200 according to another embodiment of the invention. The retainer 1200 includes a first portion 1210 and a second portion 1220. The second portion 1220 is movably coupled to the first portion 1210. Specifically, in the illustrated embodiment, the second portion 1220 is slidably coupled to the first portion 1210. The second portion 1220 is configured to slide from a first position with respect to the first portion 1210 to a second position with respect to the first portion 1210.

The first portion 1210 of the retainer 1200 defines an opening 1212 that is configured to slidably receive the tether T. The second portion 1220 of the retainer 1200 defines an opening 1222 that is configured to slidably receive the tether T. The openings 1212 and 1222 are positioned to be aligned when the second portion 1220 of the retainer 1200 is in its first position with respect to the first portion 1210 of the retainer 1200. Thus, in this first or unlocked position, the tether T may extend through the openings 1212 and 1222 and move with respect to the retainer 1200. The openings 1212 and 1222 are positioned such that they are not aligned when the second portion 1220 of the retainer 1200 is in its second position with respect to the first portion 1210 of the retainer 1200. Thus, in this second or locked position, the tether T, when it extends through the openings 1212 and 1222 is frictionally coupled to the retainer 1200. Accordingly, the tether T is fixed with respect to the body of the patient and the position and tension of the support member is maintained. In another embodiment the retainer 1200 is mounted onto the delivery tool before insertion such that the retainer 1200 can be slid onto the still attached tether directly from the delivery tool after the tether has existed the skin incision, during placement.

In such an embodiment, the second portion 1220 of the retainer 1200 may be placed in its first position with respect to the first portion 1210 of the retainer. The tether T may be passed through the openings 1212 and 1222 and the second portion 1220 of the retainer 1200 may be moved to its second position to lock or couple the tether T to the retainer.

Figure 33:
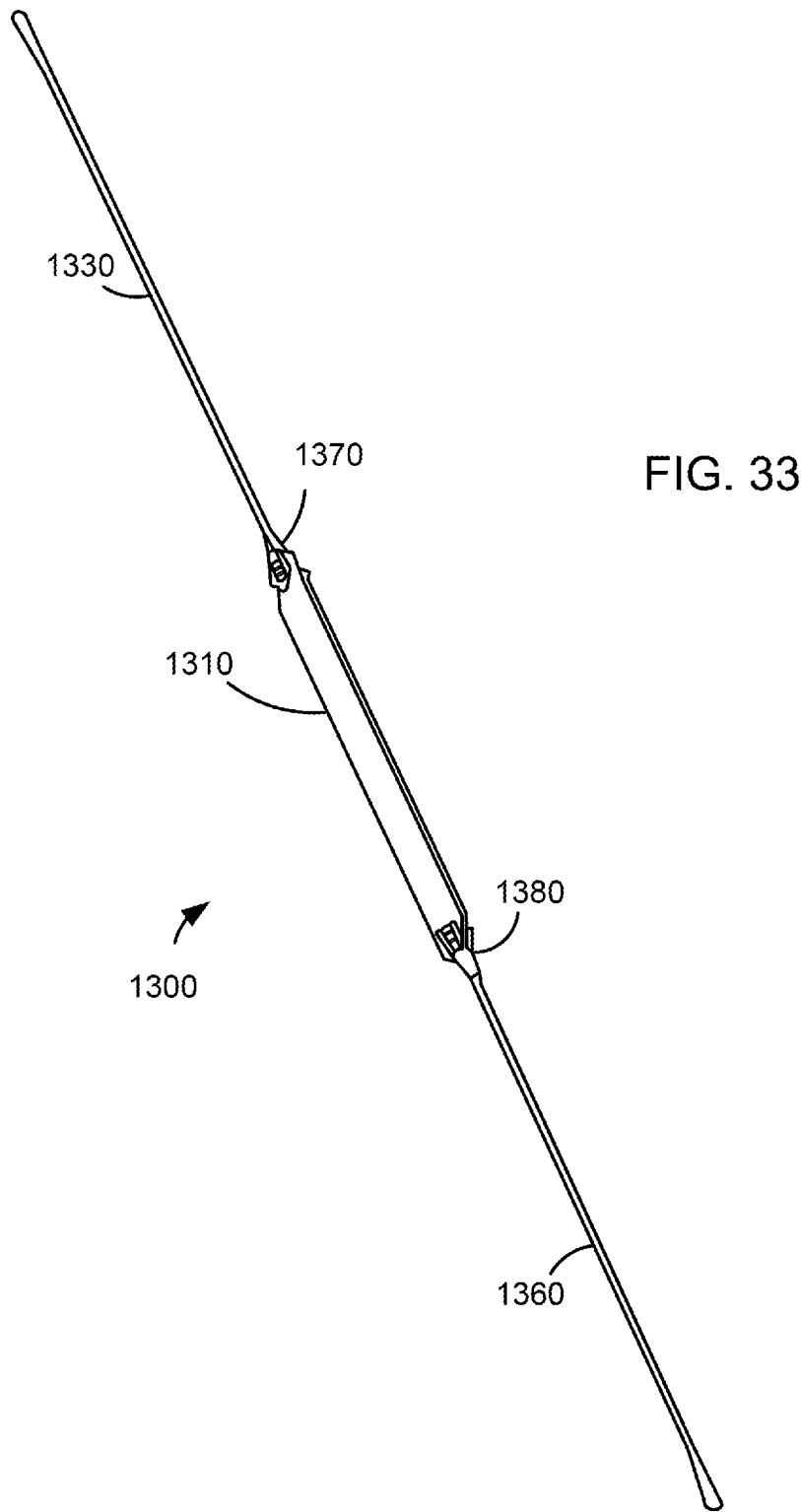
FIGS. 33-34 illustrate a support member of a medical device according to an embodiment of the invention.
Figure 34:
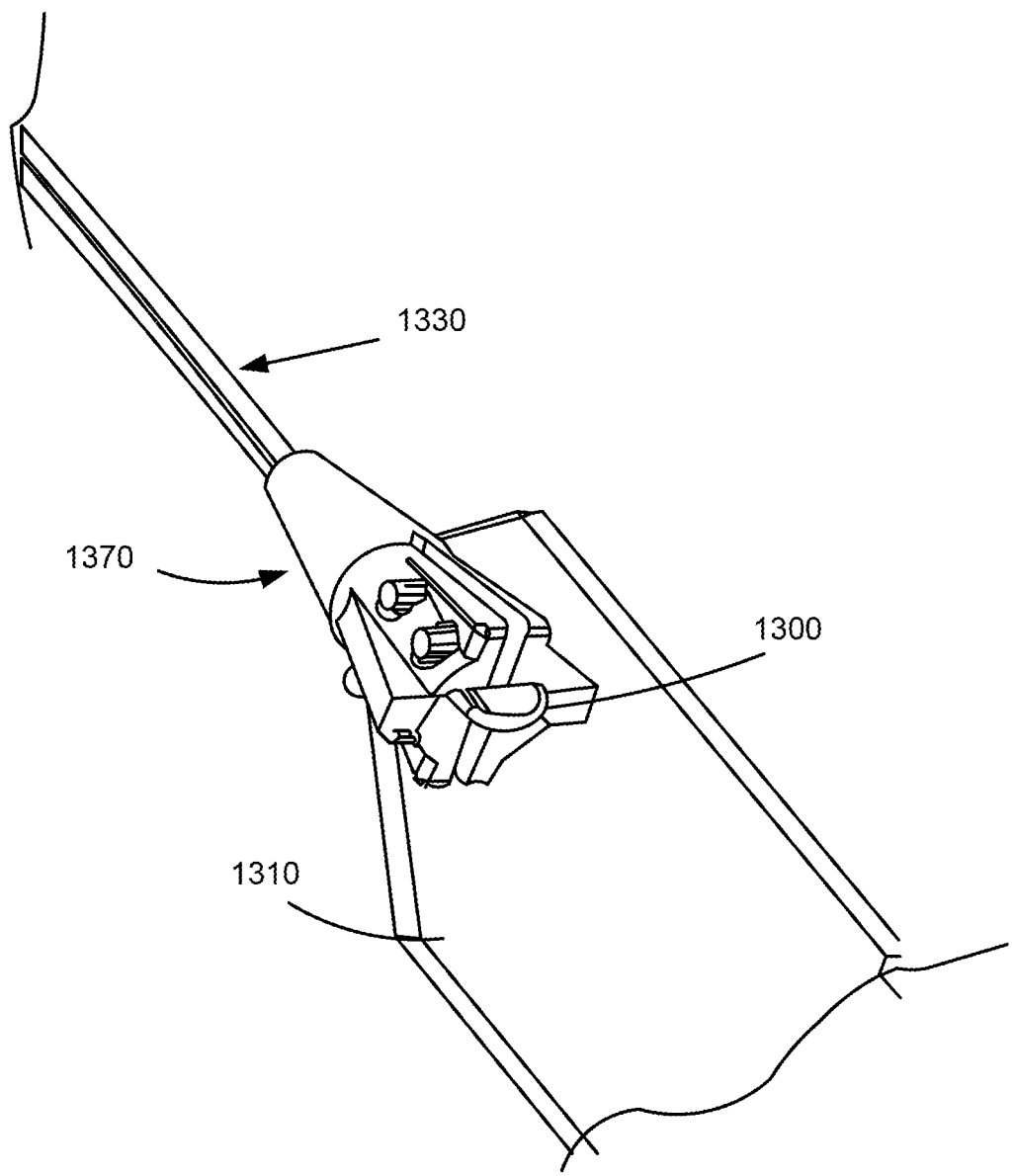

FIGS. 33 and 34 illustrate a medical device 1300 according to another embodiment of the invention. FIG. 33 is a perspective view of the medical device 1300. The medical device 1300 includes a support member 1310, a first tether 1330 and a second tether 1360. The first tether 1330 is coupled to an end portion of the support member 1310 via a coupler 1370. Similarly, the second tether 1360 is coupled to an end portion of the support member 1310 via a coupler 1380.

FIG. 34 is an expanded view of a portion of the medical device 1300. As illustrated in FIG. 34, the coupler 1370 is positioned such that the end portion of the support member is disposed between two portions of the coupler 1370. The coupler 1370 is coupled to the end portion of the support member 1310. In the illustrated embodiment, the coupler 1370 includes a retention member 1372 that is configured to help retain the support member 1310 in place within the body of the patient. The coupler 1370 may be coupled to the support member 1310 via any known mechanism. For example, the coupler 1370 may snap couple to the support member 1310. In some embodiments, the coupler 1310 is coupled to the support member via an adhesive.

In the illustrated embodiment, the tether 1330 extends through the coupler 1370 and is looped or threaded through the support member 1310. The tether 1330 may be coupled to the coupling member 1370 via any known mechanism.

Figure 35:
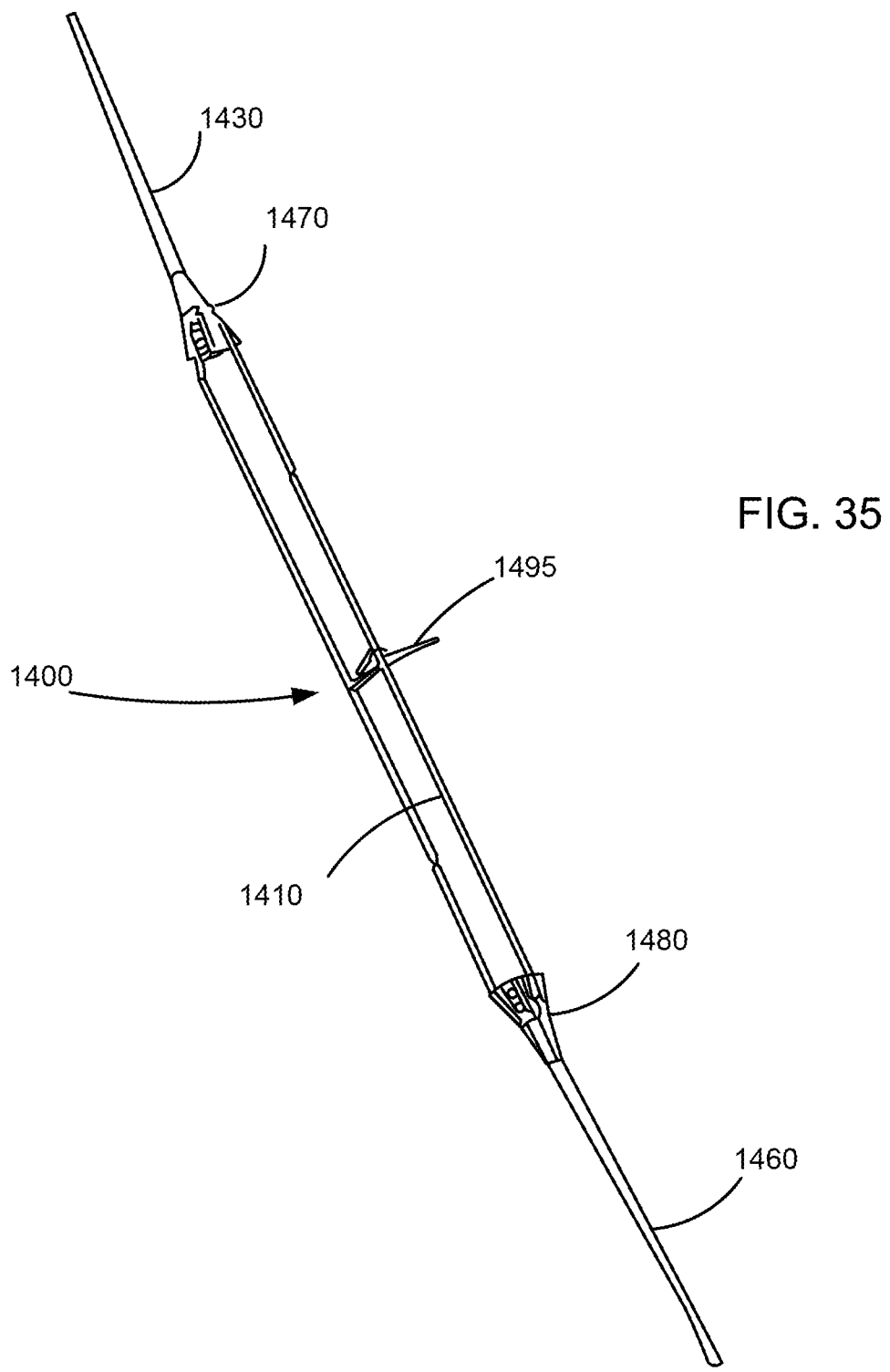
FIGS. 35-36 illustrate support members of medical devices according to embodiments of the invention.

FIG. 35 is a perspective view of a medical device 1400 according to another embodiment of the invention. The medical device 1400 includes a support member 1410, a first tether 1430, a second tether 1460, couplers 1470 and 1480, and a tether 1495. The tether 1495 is coupled to a medial portion of the support member 1410. In the illustrated embodiment, the tether 1495 is coupled to the support member 1410 across the width of the support member 1410. Accordingly, the tether 1495 may extend from the body of the patient and provide a mechanism for adjusting the tension and position of the support member 1410 within the body of the patient as described above. Additionally, the tether 1495 may be used as a centerline to facilitate the correct placement and alignment of the support member 1410 within the body of the patient.

Figure 36:
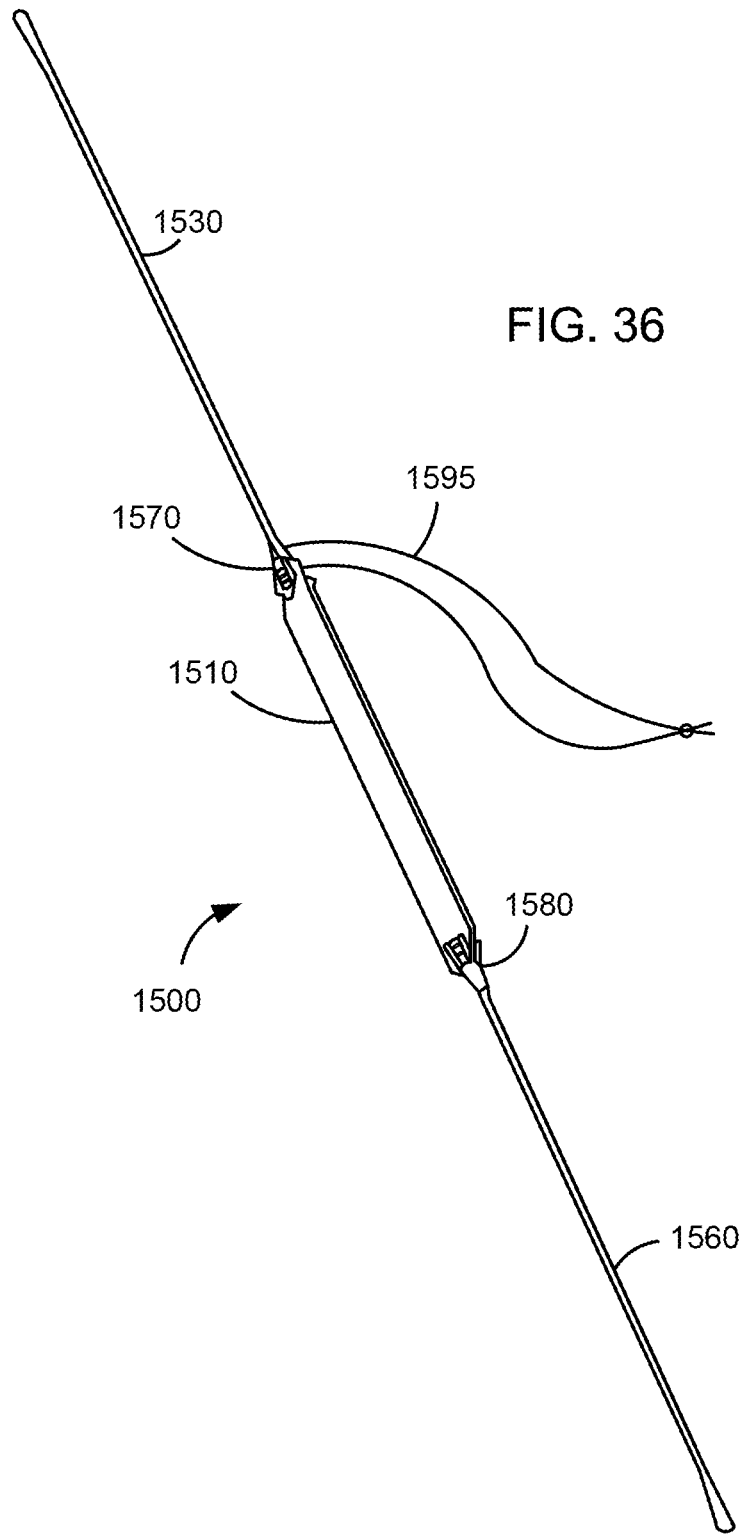

FIG. 36 is a perspective view of a medical device 1500 according to another embodiment of the invention. The medical device 1500 includes a support member 1510, a first tether 1530, a second tether 1560, couplers 1570 and 1580, and a tether 1595. The tether 1595 is coupled to the coupler 1570. In the illustrated embodiment, tether 1595 forms a loop and extends through an opening defined by the coupler 1570. The tether 1595 is configured to extend from the body of the patient (for example, through the vaginal incision) and provide a mechanism for adjusting the tension and position of the support member 1510 within the body of the patient as described above. In some embodiments, the medical device includes another tether coupled to the coupler 1580 and configured to extend from the body of the patient (such as from the vaginal incision).

A medical device includes a support member, a tether, and a retainer. The support member is configured to be placed within a body of a patient and provide support to a portion of the body of the patient. The tether forms a loop and is coupled to the support member. The tether is configured to extend from the body of the patient when the support member is placed within the body of the patient. The retainer is configured to be coupled to the tether at a first location on the tether and at a second location on the tether different than the first location. The retainer is configured to be disposed outside of the body of the patient when the support member is placed within the body of the patient.

In some embodiments, the retainer is a spooler and the tether is configured to wind around the spooler. In some embodiments, the retainer includes a lock member and a base member. The lock member is configured to move with respect to the base member from a first position to a second position.

In some embodiments, the tether is slideably coupled to the support member. In some embodiments, the tether is a first tether and is coupled to a first end portion of the support member and the implant further includes a second tether coupled to a second end portion of the support member.

In some embodiments, the tether is a first tether and is coupled to a first end portion of the support member and the implant further includes a second tether coupled to a second end portion of the support member and a third tether coupled to a medial portion of the support member.

In some embodiments, the tether is a first tether and is coupled to a first end portion of the support member. The implant further includes a second tether coupled to a second end portion of the support member, and a third tether coupled to a medial portion of the support member. The third tether is configured to extend from the body of the patient when the support member is placed within the body of the patient.

In some embodiments, the support member includes a first end portion having a first width, a second end portion having a second width, and a medial portion having a third width. The third width is greater than the first width and greater than the second width.

In some embodiments, the tether is threaded through the support member to slideably couple the tether to the support member. In some embodiments, the support member is configured to be placed adjacent to a portion of the body of the patient to provide support to the body of the patient. In some embodiments, the support member includes a first end portion having a retention member, and a second end portion having a second retention member.

A kit includes a medical device and an insertion tool. The medical device includes a support member, a tether, and a retainer. The support member is configured to be placed within a body of a patient to provide support to a portion of the body of the patient. The tether is slideably coupled to the support member and is configured to extend from the body of the patient when the support member is placed within the body of the patient. The retainer is configured to be movably coupled to the tether. The insertion tool is configured to be removably coupled to the tether and is configured to advance the medical device within the body of the patient.

In some embodiments, the insertion tool defines a lumen extending from a first end portion of the insertion tool to a second end portion of the insertion tool. In some embodiments, the insertion tool defines a lumen extending from a first end portion of the insertion tool to a second end portion of the insertion tool. The lumen is configured to deliver a fluid to the body of the patient.

In some embodiments, the insertion tool includes a coupling surface configured to engage the tether to removably couple the tether to the insertion tool.

In some embodiments, a method of placing a medical device within a body of a patient, includes (1) coupling the medical device to an insertion tool, the medical device including a support member, a tether coupled to the support member, and a retainer configured to be coupled to the tether; (2) manipulating the insertion tool to place the medical device such that the support member of the implant is disposed within the body of the patient and the tether extends from the body of the patient; and (3) coupling the retainer to a portion of the tether that is disposed outside of the body of the patient.

In some embodiments, the method includes decoupling the retainer from the tether and moving the retainer with respect to the tether and recoupling the retainer to the tether.

In some embodiments, the method includes removing the tether from the support member of the medical device.

In some embodiments, the manipulating includes, passing the insertion tool through a vaginal incision and out of the body of the patient at another location. In some embodiments, the coupling includes moving a first portion of the retainer with respect to another portion of the retainer. In some embodiments, the method includes adjusting the position of the implant within the body of the patient by applying a pressure to the tether.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
a support member configured to be placed within a body of a patient and provide support to a portion of the body of the patient, the support member including a first end portion, a second end portion, and a medial portion disposed between the first end portion and the second end portion, the first end portion, the second end portion, and the medial portion being monolithically formed as a single, continuous body, the support member including a first surface and a second surface opposite to the first surface, the medial portion having a first tapered portion that tapers towards the first end portion and a second tapered portion that tapers towards the second end portion;
a first tether forming a first loop and slidably coupled to the first end portion of the support member, the first tether being configured to extend from the body of the patient when the support member is placed within the body of the patient, the first tether being woven through one or more openings on the first end portion such that ends of the first tether extend from the first surface at the first end portion of the support member, the first loop being formed by coupling the ends of the first tether;
a second tether forming a second loop and slidably coupled to the second end portion of the support member, the second tether being configured to extend from the body of the patient when the support member is placed within the body of the patient, the second tether being woven through one or more openings on the second end portion such that ends of the second tether extend from the first surface at the second end portion of the support member, the second loop being formed by coupling the ends of the second tether; and
a third tether forming a third loop and slidably coupled to the medial portion of the support member, the third tether being woven through the medial portion of the support member at more than two locations on the medial portion of the support member such that ends of the third tether extend from the second surface at the medial portion of the support member, the third loop being formed by coupling the ends of the third tether; and a retainer configured to be coupled to the first tether at a first location on the first tether and at a second location on the first tether different than the first location, the retainer including a first slot and a second slot disposed on a periphery of the retainer, the first slot being configured to engage a first portion of the first tether, the second slot being configured to engage a second portion of the first tether, the retainer being configured to be disposed outside of the body of the patient when the support member is placed within the body of the patient, the first slot being disposed on a first side of the retainer, the second slot being disposed on a second side of the retainer at a same location as the first slot along a longitudinal axis of the retainer.

2. The medical device of claim 1, wherein the first tether is configured to wind around a middle portion of the retainer at the first slot and the second slot.

3. The medical device of claim 1, wherein the retainer includes a lock member and a base member, the lock member being configured to move with respect to the base member from a first position to a second position.

4. The medical device of claim 1, wherein the support member includes a mesh material.

5. The medical device of claim 1, wherein the retainer is substantially flat.

6. The medical device of claim 1, wherein the first end portion has a first width, the second end portion has a second width, and the medial portion has a third width, the third width being greater than the first width and greater than the second width.

7. The medical device of claim 1, wherein the support member is configured to be placed adjacent to a portion of the body of the patient to provide support to the body of the patient.

8. The medical device of claim 1, wherein the retainer includes a third slot disposed on a periphery of the first side of the retainer and a fourth slot disposed on a periphery of the second side of the retainer at a same location as the third slot along the longitudinal axis of the retainer, the third slot and the fourth slot having a depth larger than the first slot and the second slot.

9. A kit, comprising:

a medical device having a support member, a first tether, a second tether, a third tether, a retainer, and an insertion tool, the support member being configured to be placed within a body of a patient to provide support to a portion of the body of the patient, the support member including a first end portion, a second end portion, and a medial portion disposed between the first end portion and the second end portion, the first end portion, the second end portion, and the medial portion being monolithically formed as a single, continuous body, the support member including a first surface and a second surface opposite to the first surface, the medial portion having a first tapered portion that tapers towards the first end portion and a second tapered portion that tapers towards the second end portion, the first tether forming a first loop and slidably coupled to the first end portion of the support member, the first tether being configured to extend from the body of the patient when the support member is placed within the body of the patient, the first tether being woven through one or more openings on the first end portion such that ends of the first tether extend from the first surface at the first end portion of the support member, the first loop being formed by coupling the ends of the first tether, the second tether forming a second loop and slidably coupled to the second end portion of the support member, the second tether being configured to extend from the body of the patient when the support member is placed within the body of the patient, the second tether being woven through one or more openings on the second end portion such that ends of the second tether extend from the first surface at the second end portion of the support member, the second loop being formed by coupling the ends of the second tether the third tether forming a third loop and slidably coupled to the medial portion of the support member, the third tether being woven through the medial portion of the support member at more than two locations on the medial portion of the support member such that ends of the third tether extend from the second surface at the medial portion of the support member, the third loop being formed by coupling the ends of the third tether, the retainer being configured to be movably coupled to the first tether, the retainer including a first slot and a second slot disposed on a periphery of the retainer, the first slot being configured to engage a first portion of the first tether, the second slot being configured to engage a second portion of the first tether, the retainer having a first curved end extending to a second curved end along a longitudinal axis of the retainer, the retainer including a first side and a second side opposite to the first side, the first slot being disposed on a periphery of the first side of the retainer, the second slot being disposed on a periphery of the second side of the retainer at a same location as the first slot along the longitudinal axis of the retainer, the first slot and the second slot extending along a first axis perpendicular to the longitudinal axis of the retainer, the retainer includes a third slot disposed on the periphery of the first side of the retainer and a fourth slot disposed on the periphery of the second side of the retainer, the third slot and the fourth slot extending along a second axis perpendicular to the longitudinal axis of the retainer, the second axis being parallel to the first axis, the third and fourth slots being larger than the first and second slots, the insertion tool configured to be removably coupled to the first tether and configured to advance the medical device within the body of the patient, the insertion tool including a needle shaft, the needle shaft having a curved portion defining a slot on a distal end portion of the curved portion of the needle shaft, the slot configured to be coupled to the first tether to advance the support member within the body of the patient, the insertion tool including a handle, the insertion tool defining a lumen extending through the needle shaft and the handle.

10. The kit of claim 9, wherein the lumen of the insertion tool is configured to deliver a fluid to the body of the patient.

11. The kit of claim 9, wherein the insertion tool includes a coupling surface configured to engage the first tether to removably couple the first tether to the insertion tool.

12. A method of placing a medical device within a body of a patient, comprising:

coupling the medical device to an insertion tool, the medical device including a support member having a first surface and a second surface opposite to the first surface, the support member having a first end portion, a second end portion, and a medial portion, wherein the first end portion, the second end portion, and the medial portion are monolithically formed as a single, continuous body, the medical device including a first tether, a second tether, and a third tether, the first tether forming a first complete loop and slidably coupled to the first end portion of the support member, the second tether forming a second complete loop and slidably coupled to the second end portion, the third tether forming a third complete loop and slidably coupled to the medial portion of the support member, the medical device including a retainer configured to be coupled to the first tether, the retainer including a first slot and a second slot, the first slot being disposed on a periphery of a first side of the retainer, the second slot being disposed on a periphery of a second side of the retainer, the first tether being woven through one or more openings on the first end portion such that ends of the first tether extend from the first surface of the support member, the second tether being woven through one or more openings on the second end portion such that ends of the second tether extend from the first surface of the support member, the third tether being woven through the medial portion of the support member at more than two locations on the medial portion of the support member such that ends of the third tether extend at the medial portion from the second surface;

manipulating the insertion tool to place the medical device such that the support member of the medical device is disposed within the body of the patient and the first tether extends from the body of the patient; and coupling the retainer to a portion of the first tether that is disposed outside of the body of the patient, wherein the coupling the retainer to a portion of the first tether includes winding the portion of the first tether around the first slot and the second slot such that the first tether winds around a middle portion of the retainer at the first slot and the second slot.

13. The method of claim 12, further comprising:

decoupling the retainer from the first tether and moving the retainer with respect to the first tether; and recoupling the retainer to the first tether.

14. The method of claim 12, further comprising:

removing the first tether from the support member of the medical device.

15. The method of claim 12, wherein the manipulating includes, passing the insertion tool through a vaginal incision and out of the body of the patient at another location.

16. The method of claim 12, wherein the coupling includes moving a first portion of the retainer with respect to another portion of the first retainer.

\* \* \* \* \*